United States Patent [19]
Horn

[11] Patent Number: 5,946,075
[45] Date of Patent: Aug. 31, 1999

[54] VISION SCREENING SYSTEM

[76] Inventor: Gerald Horn, 1150 Heather Rd., Deerfield, Ill. 60015

[21] Appl. No.: 08/651,706

[22] Filed: May 21, 1996

[51] Int. Cl.$^6$ ....................................................... A61B 3/00
[52] U.S. Cl. ........................................... 351/246; 351/237
[58] Field of Search .................................... 351/222, 224, 351/226, 242, 243, 246

[56] References Cited

U.S. PATENT DOCUMENTS

| | | | |
|---|---|---|---|
| 3,910,690 | 10/1975 | Regan | 351/242 |
| 5,061,059 | 10/1991 | Horn | 351/226 |
| 5,263,951 | 11/1993 | Spears et al. | 606/12 |
| 5,348,551 | 9/1994 | Spears et al. | 606/5 |
| 5,565,949 | 10/1996 | Kasha, Jr. | 351/224 |
| 5,589,898 | 12/1996 | Atkinson | 351/242 |

OTHER PUBLICATIONS

Asman, et al.; Acta Ophthalmologica, Spatial Analyses of Glaucomatous Visual Fields; A Comparison with Traditional Visual Field Indices, 70(1992) pp. 679–686.

Asman et al.; Acta Ophthalmologica, Weighting According to Location in Computer–Assisted Glaucoma Visual Field Analysis, 70(1992) pp. 671–678.

Chauhan et al.; Ophthalmology, Intratest Variability in Conventional and High–Pass Resolution Perimetry, 98(1): pp. 79–83, Jan. 1991.

Damato Be. et al.; Eye, The Detection of Glaucomatous Visual Field Defects by Oculo–Kinetic Perimetry: Which Points Are Best for Screening?, 3:727–731, 1989.

Henson et al.; Ophthal. Physiol. Opt., Screening for Claucomatous Visual Field Defects: The Relationship Between Sensitivity, Specificity and the Number of Test Locations, 1988;8:123–127.

Hudson, et al.; Ophthal. Physiol. Opt., Maximizing the Dynamic Range of the Humphrey Field Analyzer for Blue–On–Yellow Perimetry 1993, vol. 13, Oct., pp. 405–408.

Lund et al. Acta Ophthalmologica, Central and Peripheral Normal Contrast Sensitivity for Static and Dynamic Sinusoidal Gratings, 61:171–82, 1983 Apr.

Poistare, et al.; Journal of Biomedical Engineering, Fully Automated Screening Procedure for Early Detection of Visual Field Defects, 8 pp. 156–161, 1986 Apr.

Shirato et al.; Japanese Journal of Ophthalmology,Subjective Detection of Visual Field Defects Using Home TV Set, 35(3): 273–281, 1991;.

Yu TC, et al.; Investigative Ophthalmology & Visual Science, Peripheral Color Contrast. A New Screening Test for Preglaucomatous Visual Loss, 32(10): 2779–2789, Sep. 1991.

Falcao–Reis et al., British J. Ophthal., Peripheral Contrast Sensitivity in Glaucoma and Ocular Hypertension, 74: pp. 712–716 1990.

Arden et al., Clin.I Vision Sci., Colour Vision Testing With A Computer Graphics System, vol. 2, No. 4, pp. 303–320 1988.

TaylorVision, Inc. Test Card (Copyright 1989).

*Primary Examiner*—Huy Mai
*Attorney, Agent, or Firm*—Banner & Witcoff, Ltd.

[57] ABSTRACT

A method for detecting the presence of eye disease in a human eye. A test subject is presented with a fixation target positioned on a colored planar surface. The test subject focuses a test eye on the fixation target and positions the test eye a sufficient separation distance from the fixation target and aligns the test eye relative to said fixation target so that the test subject's central and peripheral visual health can be tested. Additional marks are presented on the planar surface for detection by said test subject using the peripheral vision of the test eye. The additional marks are primarily the same level of black-white contrast as the planar surface but different in hue to create color contrast symbols, and are presented within the field of vision of an eye not afflicted with the disease for which testing is being conducted. In this way, the presence of eye disease can be detected if the additional marks are not visible to the test subject.

30 Claims, 19 Drawing Sheets

1. POSITION THIS SIDE OF CARD AGAINST MONITOR DISPLAY FOR ONE MINUTE
2. TURN CARD AWAY FROM MONITOR DISPLAY AND CHECK FOR SIMULTANEOUS PERCEPTION OF TEXT AND GLOW OF SQUARE BELOW

VISION SCREENING SYSTEM

BACKGROUND OF THE INVENTION

The present invention relates to a novel vision screening system. More particularly, the present invention relates to a method and related apparatus for detecting eye disease that may be easily and conveniently administered to a test subject without the need for trained personnel or specialized equipment not readily available outside a medical office.

Glaucoma and diabetic eye disease are prevalent afflictions of the eye that can occur in anyone at any time and can lead to permanent loss of vision. By far, the most common type of glaucoma is chronic simple glaucoma which is painless, slowly progressive and virtually undetectable by the individual particularly in its stages when it is most easily and successfully treated. Most individuals with glaucoma only become aware of it at a time when all that remains in one or both eyes is tunnel vision due to its gradual, painless and progressive course when left untreated. The same is true for other diseases associated with abnormalities of the field of vision, including but not limited to diabetic eye disease and certain brain tumors.

With normal peripheral vision, at any given distance from the eye, a blind spot exists at a predetermined distance just temporal to a target point at which the eye is fixated. Most of the earliest scotomas in glaucoma (i.e., small circumscribed areas ranging from dimness to completely blacked-out areas of visual field) occur in a narrow region radiating generally arcuately from just outside this blind spot above and below the point of fixation. Advanced glaucoma changes are present when multiple scotomas in this region begin to coalesce after which they extend beyond the region itself and eventually encroach on or eliminate central vision. Prior to actual loss of central visual acuity is a nonspecific decrease in central vision contrast discrimination. In early diabetes, areas in close proximity to the foveal vision develop discrete areas of tissue damage leading to receptor dysfunction or failure, often coalescing due to fluid leakage draining according to anatomical channels towards the foveal vision. Typical to early diabetes then are areas surrounding the central visual field, usually within a 10 degree cone angle, with discrete areas of tissue damage and dysfunction. These areas can continue to dim, surrounding sharp central vision, soon affecting central contrast vision, until eventually the central vision and its best acuity itself are reduced.

Most of today's methods of visual testing for peripheral vision loss from glaucoma and other diseases require sophisticated devices to accurately create a peripheral vision map, which is a graphic depiction of the extent of the field of vision, with any areas in which peripheral vision is diminished or absent well demarcated. These tests require specialized equipment, use of a trained technician, and have associated with them the problem of maintaining fixation. That is, in order to test peripheral vision, the test subject must maintain focus on a central target; failure to do so invalidates that particular peripheral vision testing sequence, and if occurring frequently enough, invalidates the accuracy of the test.

In addition, since these tests are not self-tests, the diabetic field of vision test, known as a macular, or 10 degree field of vision test, is rarely used, with preference for angiographic study of the retinal circulation, the retina being the affected tissue layer at the back of the eye in diabetes. A self-test assessing the health of the visual field as well as foveal vision could allow early awareness of diabetic eye disease within the home, prior to the permanent loss of central vision which now is frequently the earliest warning sign one afflicted with the disease will have.

One of the peripheral vision tests which has long been used, the tangent screen, is a simple test, but it too has the same fixation problem and requires a technician. Other tests of this nature include manual and automated perimetry. These visual field tests also require a technician to administer the test, and use highly specialized equipment. The patient looks at a central fixation target within a hollowed-out dome, and indicates when a light can be seen with side vision. While these tests can be very accurate, they are often difficult to administer properly since they are tedious—often taking twenty minutes or more per eye—and it is difficult to completely prevent the patient from looking directly at the source of light which is the peripheral target rather than remaining fixed on a central target and using side vision to detect the light. A trained observer views the test taker's pupil, and warns the test subject when movement of the eye is observed—the standard means of trying to maintain fixation. Such tests also typically require the use of special equipment that tends to be rather large and bulky.

About one person in five with normal visual health is unable to adequately follow the instructions discussed above to provide for useful test information. This translates to nearly one person in three in a population of glaucoma patients, where such testing is especially important for both initial diagnosis and monitoring. Of the millions of Americans at risk for glaucoma, only a relatively small fraction of this population is seen by eye professionals in a given year, and only a portion of the individuals who obtain professional assistance receive such sophisticated testing. Diabetic eye disease and glaucoma, the two leading treatable causes of blindness, are frequently first discovered after vision loss becomes sufficiently advanced to have caused permanent noticeable vision loss. Due to its gradual onset this may be misinterpreted as a glasses problem, and examination delayed. Too frequently, by the time diagnosis and treatment begins, considerable irreversible damage exists in one or both eyes, and treatment is more difficult and less vision can be saved. Earlier diagnosis and intervention before vision loss is detectable by the human eye would greatly increase the successful treatment of these diseases, and decrease the need for complex surgical intervention that is required for advanced cases.

My U.S. Pat. No. 5,061,059 entitled "Self-Detection Glaucoma Test Method," which is incorporated into this disclosure by reference, describes a novel method test method for self-detection of eye disease. Indeed, the test method described in my patent is relatively easy and convenient to use without the need for expensive equipment or a technician.

An improved test method, however, might further enhance the ability to test for eye disease with improved accuracy, allow assessment of central as well as peripheral visual health, improve fixation compliance, provide testing instructions in a convenient manner, provide for self-demonstration, interactive test subject training, and interactive review of test-taking proficiency. Further, an improved test method might, at the same time, be easy to use, convenient, and relatively entertaining. It is therefore an object of the present invention to provide an improved eye disease self-test method that further enhances the ability to detect eye disease and is also easy to use, convenient, and relatively entertaining.

Other objects and advantages of the present invention will become apparent from the ensuing description.

SUMMARY OF THE INVENTION

The present invention is directed to a novel test method and devices for detecting the presence of eye disease in the human eye, such as glaucoma or diabetic eye disease for example. The inventive method provides an easy to use and convenient test method for sensitive detection of early eye disease that can be conducted either inside or outside the medical office using equipment that is readily available to the average consumer.

The present invention provides a sensitive and accurate method for detecting the presence of eye disease in a human eye wherein a test subject is presented with a fixation target positioned on a colored planar surface. The test subject focuses a test eye on the fixation target and positions the test eye a sufficient separation distance from the fixation target and aligns the test eye relative to said fixation target so that the test subject's peripheral vision can be tested. Additional marks are presented on the planar surface for detection by said test subject using the peripheral vision of the test eye. The additional marks are of a low color contrast relative to the background planar surface to create low color contrast symbols, and are presented within the field of vision of an eye for which testing is being conducted. In this way, the presence of eye disease can be detected if the additional marks are not visible to the test subject.

The preferred test method can be administered with the aid of a home personal computer system, or video equipment such as a television and video cassette player or the like. In this way the test may be conducted in an environment that can provide the test subject with appropriate instructions and guidance to help ensure that the test format and procedure is clear to the test subject throughout the entire test. The test method may also provide for quick and easy review of the test results so that the test subject may be presented with an indication of the test subject's risk of disease. Further, the preferred test method may includes new devices and procedures for proper positioning of the test subject relative to the test field, as well as devices and procedures for assisting the test subject in adjusting the testing room lighting to an appropriate level, procedures to monitor the test subject's compliance with testing procedures, and devices for monitoring and enforcing the test subject's point of fixation.

BRIEF DESCRIPTION OF THE DRAWING

A preferred embodiment of the present invention is described herein with reference to the drawing wherein.

DESCRIPTION OF THE PREFERRED EMBODIMENT

The preferred embodiment of the present invention is a color vision and peripheral color contrast field threshold test that is embodied in interactive computer software. Specifically, color vision and color contrast techniques are used to test a relatively large number of cone, or color, receptors at and above threshold for peripheral vision. Small color contrast differentials are presented to the test subject using relatively large, flashed symbols 8 to test for loss of peripheral color contrast discrimination. Threshold is a function of degree of color contrast discriminated rather than test symbol size.

Peripheral field testing using contrast methods is not new. Sinusoidal gratings for contrast sensitivity testing of the visual field, blue stimuli on yellow backgrounds, and low color contrast testing using the peripheral ring of Arden, for example, have all been used previously with success. Color testing may use a less robust system involving a lower volume of neural pathways, and provide an earlier indicator of disease. Blue on yellow testing combines some of these potential advantages, but typically tests threshold with variation of stimulus size. The yellow background isolates blue cones, but the ability of blue cones to detect stimulus size may not be as sensitive as testing further for color discrimination as a threshold measure.

The vision screening system described herein attempts to go yet a step further by testing cones for color discrimination which have been background adapted. It is believed that such testing can be more sensitive than stimulating cones with an easily-detected wavelength to which the test subject had no previous adaptive exposure. Certain advantages may therefore be obtained by testing the peripheral field based on the test subject's ability to detect flashed symbols of incrementally-varied color relative to a colored background. Preliminary testing of this system suggests, for example, great sensitivity for detection of diabetic eye disease and glaucoma.

Indeed, test results indicate that the highly localized discriminative testing of peripheral loci in accordance with the present invention creates a sensitive self-test. There is a considerable reduction in ability to detect color contrast of specified levels in even early eye disease compared to age-matched normals. This allows selection of points just above such thresholds as part of a self-test that can sensitively detect early eye disease. Further, such points could be age adjusted. Indeed, tests conducted in accordance with the present invention demonstrate a considerable difference in discrimination between normals and most early glaucoma patients. To allow effective self testing, this sensitivity is quantitized and converted in the preferred embodiment of the present invention to a score, to provide an effective pass/fail/borderline/retest screening test format.

Figure 1:
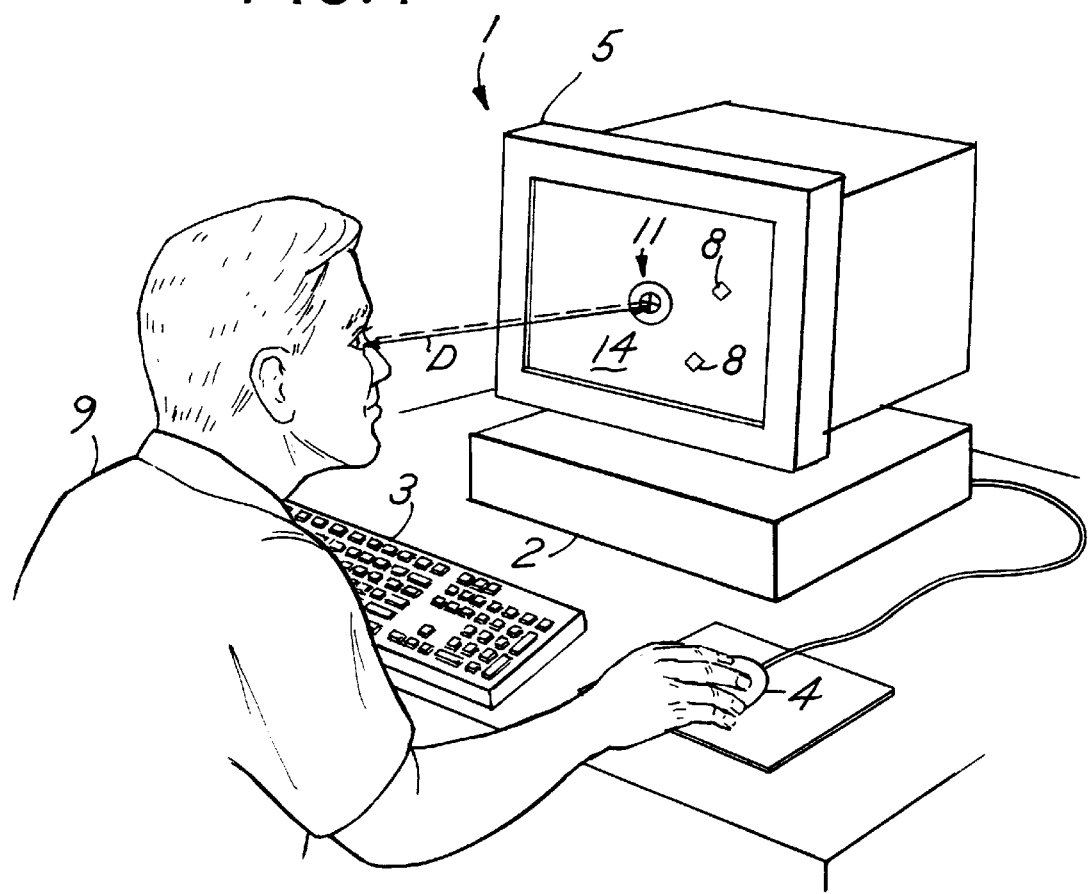
FIG. 1 is a perspective view of a test subject engaging in a test program in accordance with a preferred embodiment of the present invention.
Figure 2:
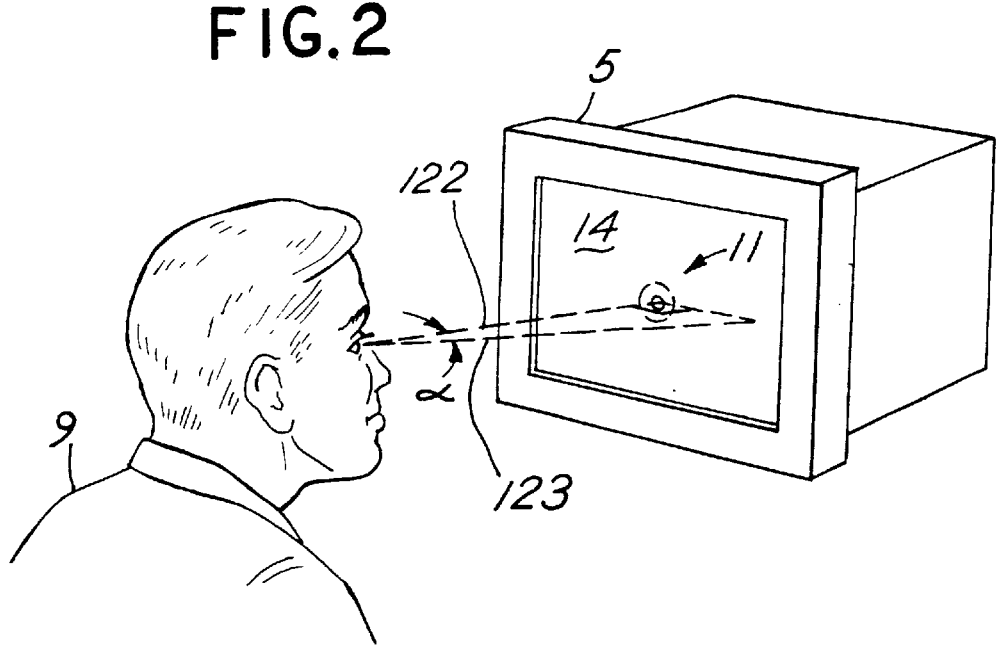
FIG. 2 is a second perspective view of a test subject engaging in a test program in accordance with a preferred embodiment of the present invention.
Figure 3:
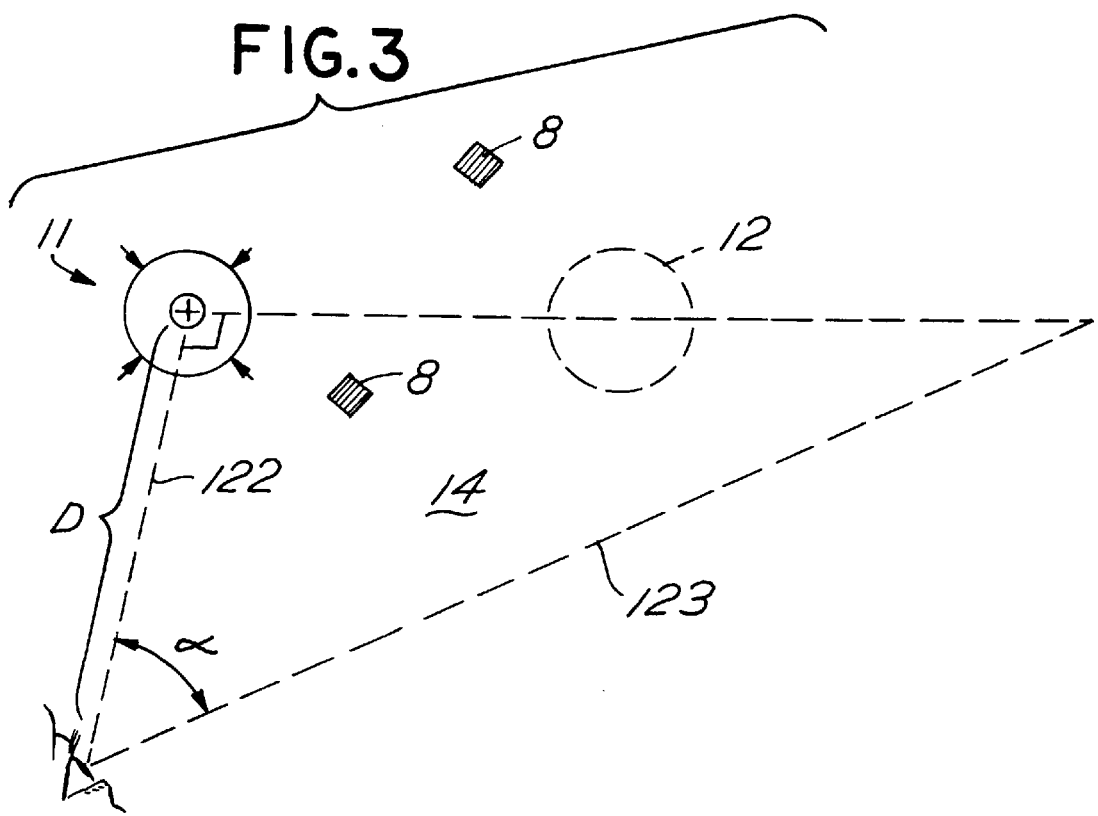
FIG. 3 is a view of the test field showing a fixation target and two test symbols, and identifying the blind spot region.
Figure 4:
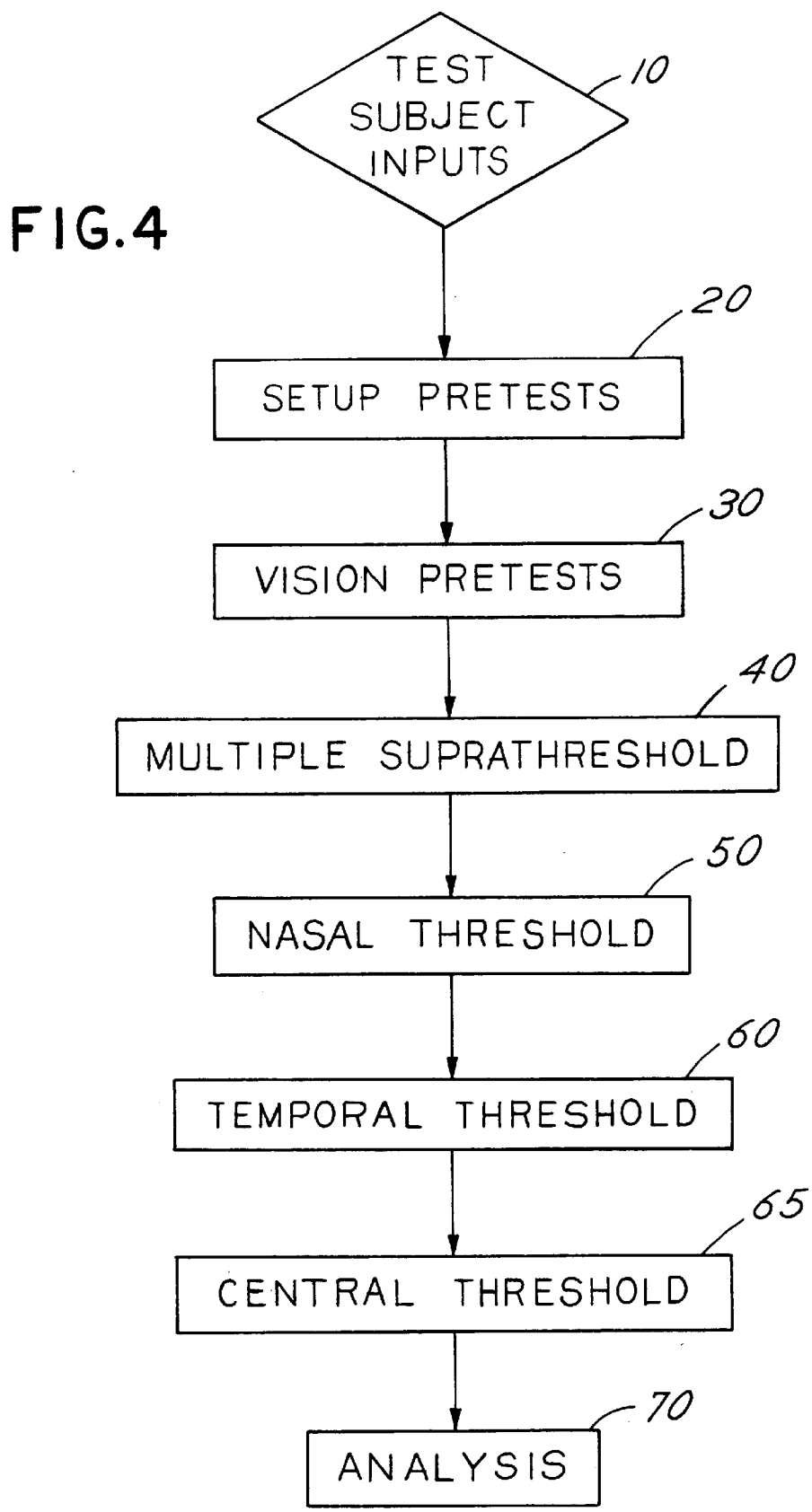
FIG. 4 is a chart illustrating generally the overall flow of the test program of the preferred embodiment of the present invention.

The preferred color vision central and peripheral color contrast field threshold and suprathreshold test is conducted using conventional computer equipment, such as a home personal computer system 1 for example. As shown in FIG. 1, the computer system 1 preferably includes a CPU 2 providing higher level sound and graphic capabilities (including, for example, a video card that provides 32,000 or more colors), a keyboard 3, a computer mouse 4, and a high-resolution color monitor 5 having, for example, 600× 800 pixel resolution. It will be understood, however, that the present invention can also be carried out using other more conventional video equipment, such as a television display monitor and video tape or laserdisk player, interactive 32-bit game cartridge, or the like.

The preferred test program combines the merits of sensitivity of low color contrast testing with geometric symbols 8 positioned throughout the visual field to result in a map 120 of the color contrast sensitivity of the test subject's field of vision. In particular, the preferred test program tests a field where α is about 27 degrees (nasal test) and 25 degrees (temporal test), whereby approximately 100 grid points are tested. The preferred test program allows the locations of the particular points tested to be adjusted if desired.

The preferred test program begins by soliciting and recording the age and/or birth date of the test subject 9 at step (10). As with most visual field testing, there is a decline in symbol recognition, that is color contrast detection ability, that correlates well with age. The preferred embodiment uses two methods to accurately account for this change. First, five separate sets of test symbols are used: one set for ages up to 50; a second set for ages between 50 and 55 (with increased color contrast by one increment, as defined below); a third set for ages between 55 and 70 (with increased color contrast by yet another increment); a fourth set for ages 70 to 85 (with increased color contrast by yet another increment); and finally a fifth set for ages over 85 (with again an increased color contrast by yet another increment). Second, scoring is adjusted based on age, and statistical comparisons that have been made with normals and early glaucoma patients for example. The age of the test subject is considered in the analysis portion of the test program at step (70) for the purpose of more accurately screening for the presence of eye disease. Age adjustments were determined using a professional prototype test to quantify color contrast thresholds at each grid test point to construct threshold points. Whereas the conventional definition of threshold is detection in 50% trials, the steep threshold curve observed for this test, and the desire for a screening test, led to incorporation of points representative of detection in about 95% of trials.

Other preliminary information may be recorded at step (10), such as the patient name, patient sex, test date, test time, and test version number. The filename in which the test results will be stored may also be noted for the test subject 9.

The preferred test program continues whereby the test subject 9 is given the opportunity to select one of three possible test format; a first test format that tests the left eye, a second test format that tests the right eye, or a third test format that tests both eyes. Alternatively, the default may be for the test program to test both eyes without giving the test subject an option.

The test subject 9 then practices following a moving or "floating" fixation object 11 that moves alternately about 100 pixels vertically and horizontally in a repeating fashion. In particular, the test subject 9 is required to move the cursor 125 associated with a computer mouse 4 in synchronization with the moving fixation object 11. The test taker 9 is placed a predetermined initial distance D using for example a measuring tool or distance prop, as discussed further below, such initial distance varying depending on the particular monitor 5 size in use. The blind spot of the test subject 9 is then determined using a peripheral target 29 that slowly travels temporally away from the fixation target (step (100). The distance D is adjusted so that the blind spot of the test subject 9 is affixed in the same relative position on the computer monitor 5 for every test taker 9, allowing the 27 degree field (nasal test) and 25 degree field (temporal test) to be obtained. If no blind spot is found, the test repeats slightly below and then slightly above the fixation object 11. Once the blind spot is identified, the test taker is instructed to adjust the distance prop a specified number of units, and then to use the distance prop to accurately position the test subject 9 in front of the computer monitor 5.

Figure 11:
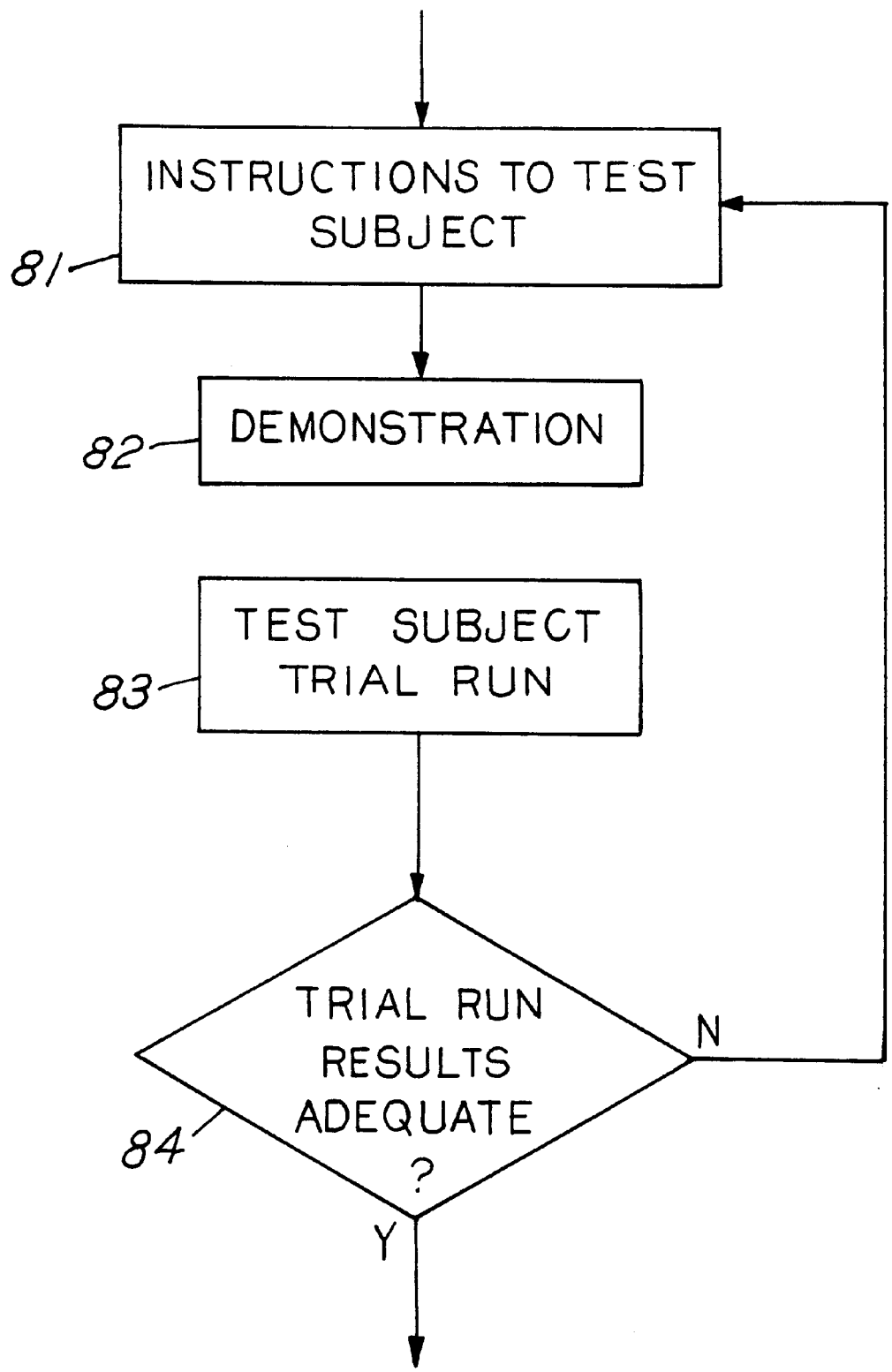
FIG. 11 is a chart showing generally the preferred flow of the interactive test subject instruction provided by the preferred embodiment of the present invention.
Figure 12:
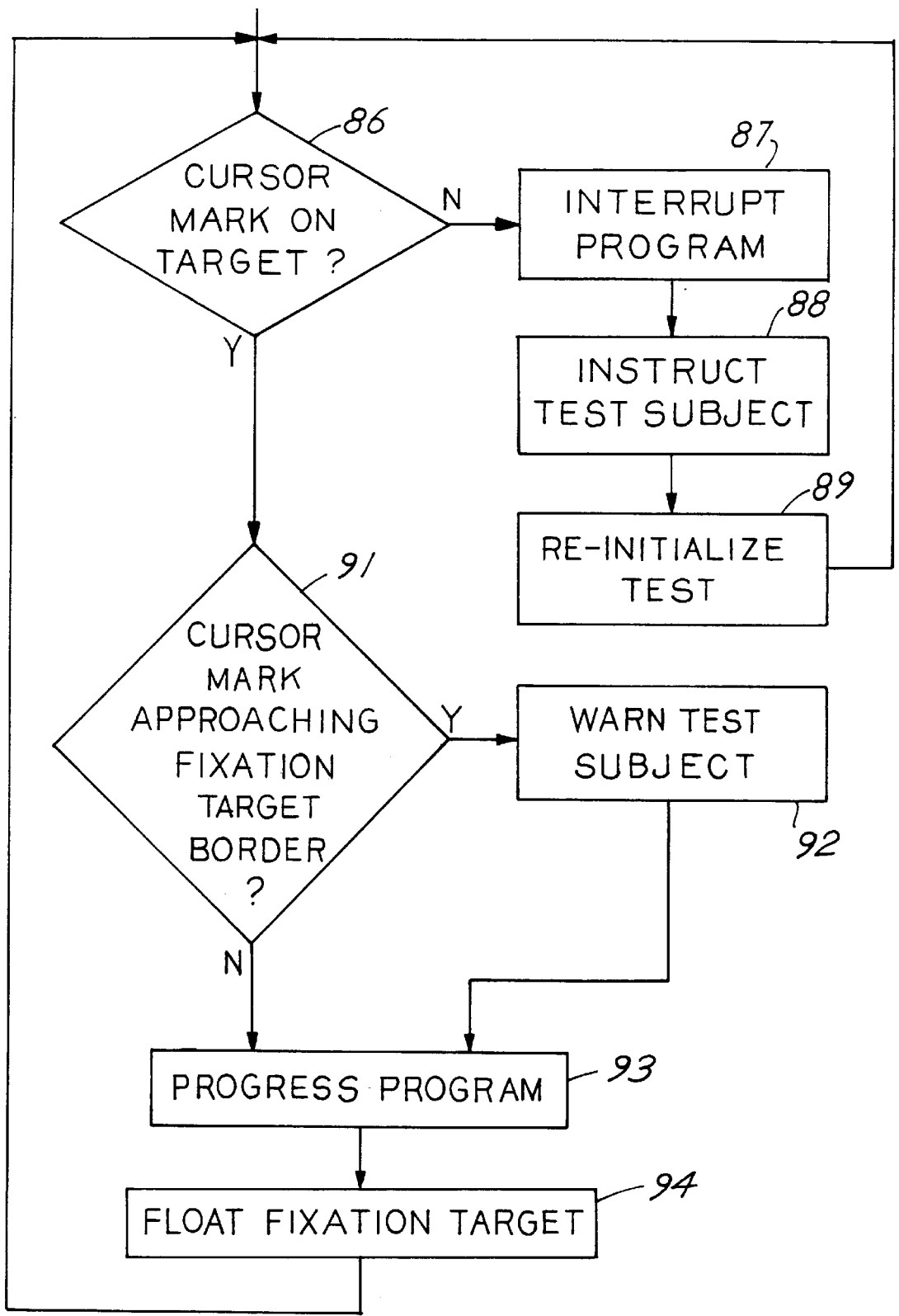
FIG. 12 is a chart showing generally the preferred flow of the fixation detector aspect of the present invention.

As shown for example in FIG. 11, these or other similar instructions are coupled with demonstration and optional trial runs whereby the test subject 9 is given the opportunity to become better acquainted with the particular test format and requirements. The test program may monitor and interact with the test subject 9 during this time to provide the tailored guidance that the test subject 9 appears to require to become sufficiently comfortable with the testing format and requirements. Such guidance may include instructions (81), demonstrations (82), and/or trial runs (83) that are repeated as interactively deemed necessary (step 84). Any instructions and/or other notices (81) intended to be delivered to the test subject 9, either before, during, or after testing, may be provided in the form of printed materials, or may be presented to the test subject using text, graphics, video, speech and/or other audio representations generated using the graphical and audio capabilities of the computer system 1.

The preferred test program is based on a theme that is intended to make the test program more entertaining and less intimidating for the test subject 9. A more relaxed and comfortable test subject 9 is likely to result in more accurate test results. Moreover, test subjects are more apt to conduct a self test if the testing environment is friendly and entertaining.

The preferred test program generally calls upon the test subject 9 to identify the appearance of various colored targets, or marks 8, that are momentarily displayed, or flashed, at various locations on the test field 14 on the computer monitor display 5. The target flash is preferably for a period of approximately 50 milliseconds. To keep with the theme of the test program, the various targets or marks 8 may be represented as objects, such as "quarks," "antiquarks," satellites, planets, spaceships, or the like traveling through space for example. Throughout the test program these marks 8 appear, either alone or in combination with others, at various locations on the test field 14 displayed on the computer monitor 5.

These marks 8 preferably have a generally annular diamond shape or a solid diamond shape. The marks 8 constitute a region of color that is contrasted against the color of the test field, or background 14. In this way the marks are low color contrast symbols 8, or for example, are regions that have a change in the proportion of the primary additive colors that constitute the background 14, so to create small increments of detectable change in color. The degree of contrast used to develop the test range included 17 contrast increments as follows: 3%, 5%, 7%, 10%, 15%, 20%, 25%, 30%, 40%, 50%, 60%, 70%, 80%, 100%, 120%, 140%, and 200%. Color hue was set using rgb values, and programs measuring color contrast. There is not necessarily any significant difference in luminance, or black/white contrast, between the mark 8 and the background 14 for most test symbols 8. There is increased luminance, however, in the preferred embodiment for increments beyond 100% contrast.

The presence of a flashed object reaching a peripheral receptor is discriminated most easily as having color contrast relative to a colored background by healthy receptors. In the presence of various eye disease these receptors lose sensitivity to detect color, color contrast, and white light on a white background. All such symbols, and more, can be used to sensitively test for peripheral vision health. The present invention uses peripheral color contrast as a readily available and accurate method for use with personal computers, television monitors, interactive game cartridges, video conversion, and the like.

Specifically, the test program tests the subject with non-varying 90 mm$^2$ targets 8 of varying color contrast. For most test increments this means varying rgb values relative to the background so that the luminance is constant but the hue—the rgb components—is varied, in contrast to more conventional visual field tests which typically present targets of varying size. The flash speed for the presented symbols 8 of the preferred test is a constant, and the targets 8 presented are all the same size. It is rather the color contrast relative to the background 14 that determines threshold and ability to distinguish the symbol 8 from the background 14.

While the center of each target 8 is spaced no closer than approximately 1.5 degrees of field separation, due to the size of the test symbol 8 and reliance on color contrast for the detection variable, the test areas nearly abut one another. At threshold, the preferred test program tests a larger retinal area than conventional tests that vary stimulus size using a target of 90 mm$^2$ on a 17" monitor versus 7 mm$^2$ for a typical 3 mm diameter white test symbol on a Humphrey 24-2 rather than color contrast. Further, the presentation of such color contrast symbols 8 in a momentary flash appears to be quite significant, insofar as a first target that differs from a second target by only 3–5% color contrast will be discerned with greater difficulty as the flash time becomes shorter. The color contrast symbols 8 may be used alone, or in combination with black and white, or luminance, contrast symbols 8. The preferred test program, however, employs only color contrast symbols 8. Indeed, the peripheral targets or marks 8 have a decrease in blue saturation and are displayed against a purple background 14 (rgb value 153 0 153). The color contrast presented by this color combination is deemed to provide enhanced sensitivity to the test. An alternative color axis for color contrast may be used, such as in the television monitor embodiment for example, whereby the marks 8 are increased in blue saturation and displayed on background 14 that is 0 153 153. A background 14 of two primary additive colors could represent yet another axis. It appears as though such color contrast combination also provides effective sensitivity to the test. All three color axis can be also be used effectively in this manner (red-blue/purple background; blue-yellow/green background; red-yellow/orange background).

PRETEST

The preferred test program begins with a short series of individual pretests (20) and (30) that are conducted to help the test subject 9 assess and/or adjust the testing environment for maximum effectiveness. These pretests consist of setup pretesting and a vision "pretest." The setup pretests (20) include monitor adjustment and calibration (21) and lighting adjustments (23). The vision pretests (30) include a first blind spot pretest to make an initial adjustment for test subject-to-test field distance (27), a second blind spot pretest to double-check the blind spot location (31), and a color contrast acuity measurement (35), useful as a general measure of visual health. The preferred test program has an option for adjusting the symbol sensitivity (degree of color contrast) (39), either manually or automatically in response to the color contrast acuity measurement (35), to recalibrate the color contrast used with the particular test subject 9 so as to provide added flexibility to, for example, monitor the foveal vision of the test subject. The inputted age of the test subject, from step 10, is also preferably used to calibrate the color contrast sensitivity used during the test program.

For example, a first setup pretest (21) helps the test subject adjust the color, contrast, and brightness of the computer display monitor 5. As shown in step (22), these variables may be adjusted with the aid of standardized colors and gray scales, which may be provided to the test taker as part of a brightness standardization for ambient light as a software adjustment, or on cardboard strips for example, against which the color and brightness displayed by the monitor 5 are compared.

Figure 22:
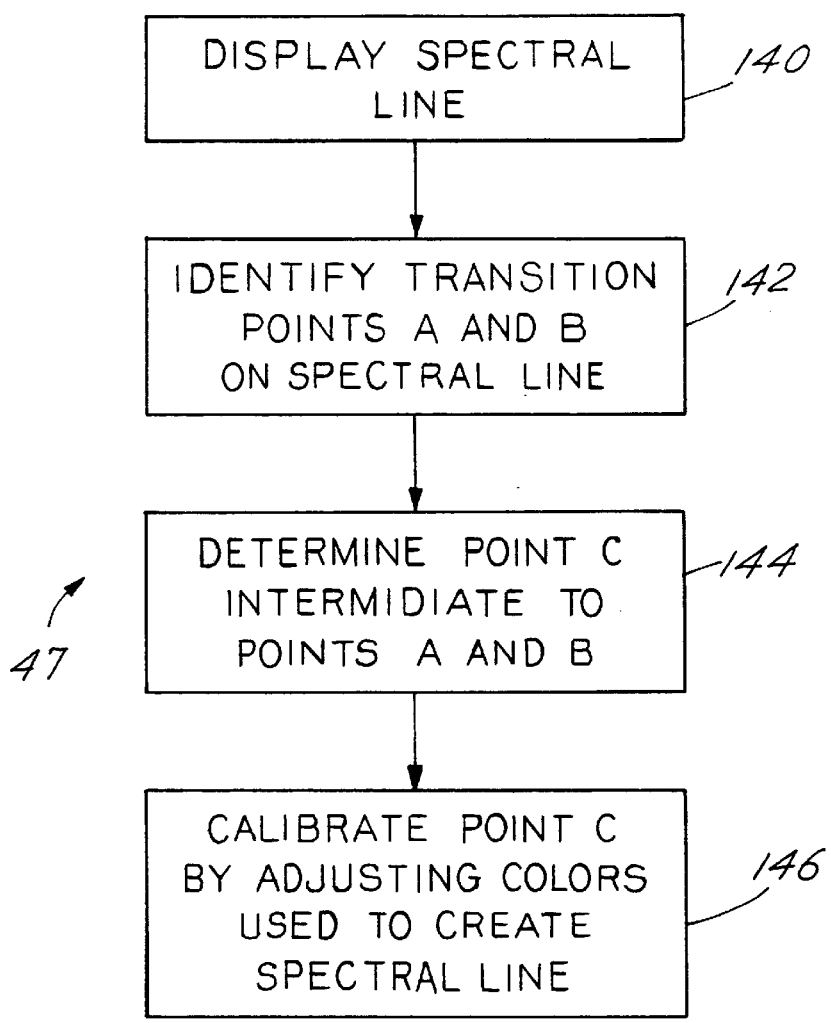
FIG. 22 is a chart showing generally the preferred flow of the display monitor color calibration procedure of the present invention.
Figure 23:
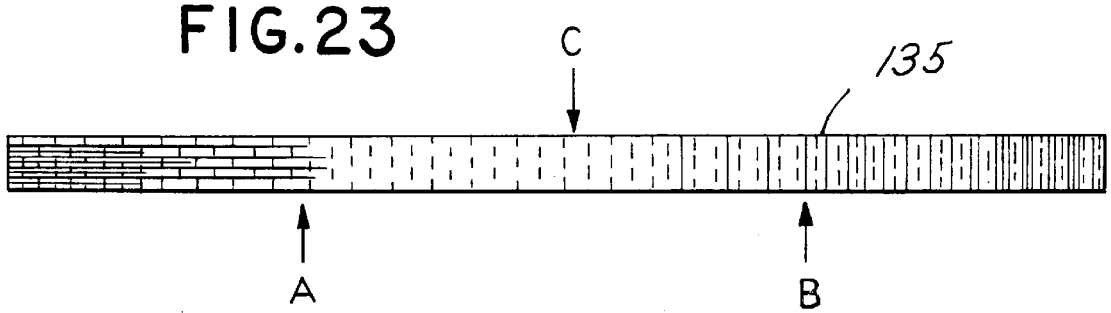
FIG. 23 is a color spectral range line that is used in the preferred program to help color calibrate the display monitor.

Preferably after the contrast and brightness of the monitor 5 are adjusted, another setup pretest (47) may be used to calibrate the colors displayed by the monitor 5. The preferred calibration procedure is set forth in FIG. 22 for example. Instead of using costly or specialized hardware or software to adjust the colors displayed by the monitor 5, monitor color is adjusted in the preferred embodiment of the present invention through the use of a finely incremented horizontal line 135 that is displayed on the computer monitor 5 (step 140), as is shown for example in FIG. 23. The horizontal line 135 provides a color spectral range from "bluish purple" on one end of the spectrum, to a "reddish purple" on the other end of the spectrum. Hues vary from about 250–350 in single increments, wherein a hue of 300 is equal to an rgb value of 153 0 153.

The test subject is advised to view the horizontal line 135 for the purpose of identifying two locations on the line 135; (1) the location where the test subject perceives a spectral change from a "bluish purple" color (more purple than blue) to a mostly blue or dominantly blue color (point A); and (2) the location where the test subject perceives a spectral change from a "reddish purple" color (more purple than red) to a mostly red or dominantly red color (point B). These two locations may be identified (step 142) by the test subject using a cursor mark under the control of the computer mouse 4 for example.

Once the two locations have been identified by the test subject, the preferred program bisects the two selected locations (A) and (B) along the spectrum to identify the spectral point (C) that is considered the truest color purple—equal parts blue and red—as displayed on the particular computer monitor 5 being used (step 144). This point may shift dramatically from a high Kelvin (temperature setting of a monitor), i.e. 9300, to a low Kelvin, i.e. 5000, and gradations in between. Addition or subtraction of blue across the entire spectrum, for example, can then result in a controlled shift along the length of the spectrum of the equally balanced (red versus blue) violet region (C) to a predetermined point that is a constant for all calibrations (step 146). In this manner the relative settings from one monitor to another monitor will vary only negligibly.

In a similar manner, a finely incremented horizontal line displaying a spectral range from "greenish yellow" to "reddish yellow" can be displayed and adjusted, to more completely calibrate the monitor. The preferred program thereby can detect the relative gains of both green and blue relative to red, and the information is then used to adjust the relative settings of blue and green relative to red for all colors within the color palette of the vision test. No color match swatches or the like need be used.

If desired, the test program may first present to the person calibrating the monitor 5 a display of all 17 contrast increments used by the test program, so as to help check whether the person calibrating the monitor 5 can perceive the various contrast increments. This operation helps to provide appropriate monitor color calibration.

A preferred method to control ambient light (23) uses a card 6 with luminous material 7 adjacent to high contrast print 28, functioning effectively as a light meter. The card 6 is optionally provided with the preferred test program materials to help the test subject 9 adjust the lighting in the testing room to an appropriate level. The testing room should not be either too dark or too light. The preferred light meter comprises a light-colored card 6 constructed from cardboard that has a spot approximately one inch in diameter of luminescent material 7, such as luminescent paint for example, located in the center of one side of the card 6. Printed in fourteen point bold print on the light-colored margin surrounding the luminescent material 7 are instructions 28 that advise the test taker 9 to first position the luminescent side of the card 6 against or adjacent the display portion of the computer monitor 5 for a specified period of time (24). During this time the luminescent material 7 absorbs a sufficient amount of light radiation to allow the material 7 to glow in lower light levels. The test subject 9 is next instructed to turn the luminescent side of the card 6 away from the computer display 5 (step 25), and to adjust the lights for simultaneous perception of a glow of the luminescent material 7 and visibility of the printed instructions 28 on the card 6 (step 26). It will be understood that other appropriate symbols may be used on the card for this purpose instead of the printed instructions. The resulting control of light level range in the testing room will enhance the overall accuracy of the test program results. Alternatively, the appropriate lighting levels can be set with the aid of a photodetector. The preferred light level for the testing room is sufficient to barely read the luminous dial of a watch.

The vision pretests commence with a first blind spot pretest (27) that identifies the monitor size and recommends a starting distance for the test subject 9 to begin testing. The accuracy of the screening test of the present invention is maximized if test subject 9 is properly positioned in front of the testing field 14. An initial distance of 14" between the test field and the test subject is recommended for a standard 17" monitor 5. This initial distance is increased proportionally for larger monitors. At these distances, the preferred test program tests a field where $\alpha \approx 27$ degrees (nasal test) and 27 degrees (temporal test); 15 horizontal increments with approximately 1.7 degrees each.

Proper positioning of the test subject 9 in front of the monitor 5 can be approximated using a measuring tape or an alternative measuring tool or distance prop. Alternative distance props may include, for example, a specified length of nested foam drinking cups that bridge the gap between the test subject's upper chest region and the test field 14.

Another alternative measuring tool 13 may comprise a modified eyewear frame 15 wherein the bridge portion of the frame includes a one-inch vertical slit 19 to accept a string 16. One end of the string is affixed adjacent to the test field 14, such as through the use of a flat plate 18 secured to the display monitor 5, using adhesive tape, a latch and hook material arrangement, or the like, either above or below the test field 14. The string 16 includes a series of numbered or color-coded protuberances 17 spaced approximately one inch apart, which allow the string 16 to be securely snapped and retained in position on the eyewear 15 at varying lengths. In this way a specified length of string 16 can be secured to the eyewear 15 so as to, when worn by the test subject 9 such that the string 16 is relatively taught, provide an approximate separation distance D required for the selected display monitor size. A correlation between the selected display monitor size and the appropriate protrusions 17 to be used to secure the string 16 to the eyewear 15 can be provided to the test subject 9.

Instead of requiring the use of a distance prop, an alternative initial blind spot pretest incorporates a stationary blind spot color contrast symbol 8 that flashes within region 12 of the test field 14. The test subject 9 appropriately positions himself or herself in front of the test field 14 such that the flashing symbol 8 is within his or her blind spot and can no longer be perceived. In this way the test subject 9 is properly positioned for the testing and can be analyzed against data obtained from normals.

More accurate refinement of the starting distance D of the test subject 9 from the test field 14 is accomplished through a second blind spot identification pretest and position adjustment (31). Like the first blind spot pretest (27), the second blind spot pretest (31) can be repeated at any point in the test program, if desired, to ensure that proper placement of the test subject 9 is maintained throughout the test program. The purpose of the second blind spot test (31) is to help ensure that nasal margin of the blind spot is affixed to the same region 12 of the screen for each test taker, each time the test is taken. This improves test consistency, and allows testing of a central field where a is 20–25 degrees, and a peripheral field where α is about 27 degrees when the fixation target, or fixation detector 11, is moved off center. Moreover, placement of the region 12 at one-quarter the distance across the width of the display of the monitor 5 allows a 25-degree field to be tested when the fixation detector 11 is placed in the center of the display.

Vision Fixation Detector with Fixation Enforcement

It is widely known that proper fixation of a test subject is a critical element to any side vision test. The preferred test program attempts to capture the concentration and focus of the test subject 9 during the course of testing by requiring the test subject 9 to position and maintain a cursor mark 99, the position of which is controlled through the test subject's manipulation of the computer mouse 4, within the region of the fixation detector or target 11.

Figure 16:
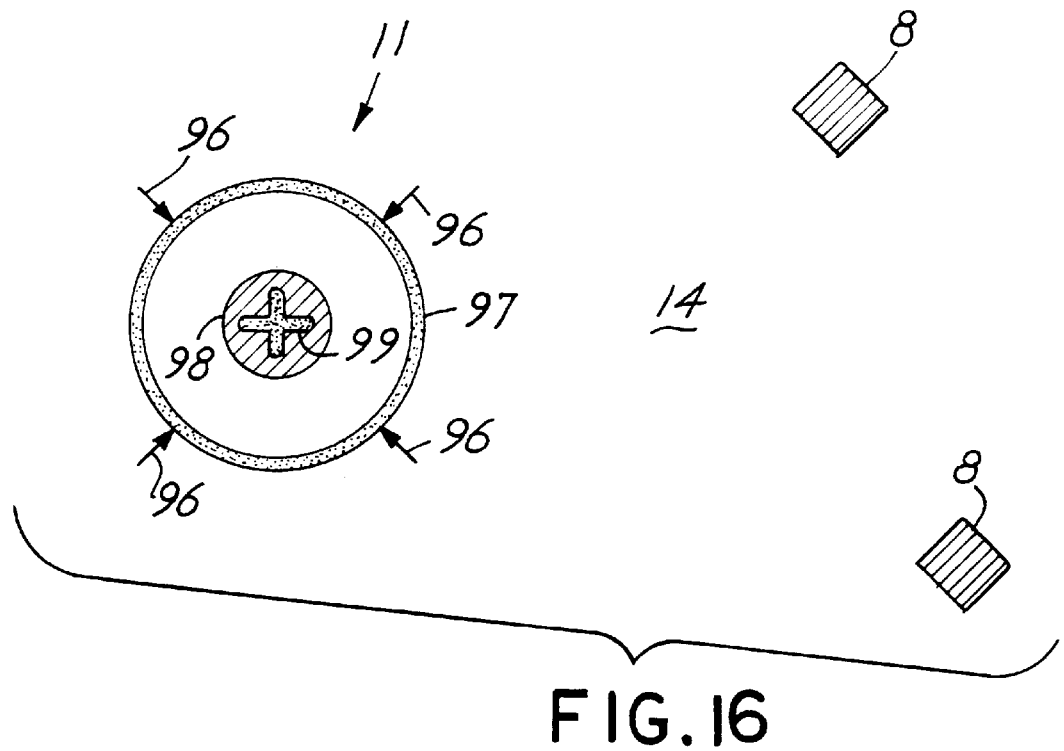
FIG. 16 illustrates the preferred fixation target in the multiple suprathreshold test having two targets momentarily flashed on the planar surface, and a cursor mark properly positioned within the fixation target to allow progression of the test.
Figure 17:
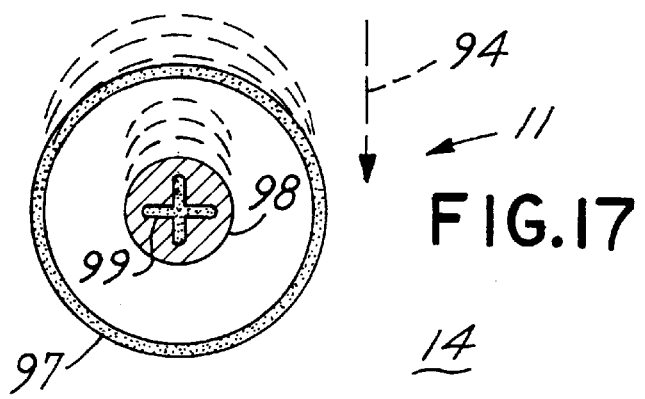
FIG. 17 illustrates example floatation of the fixation target.
Figure 18:
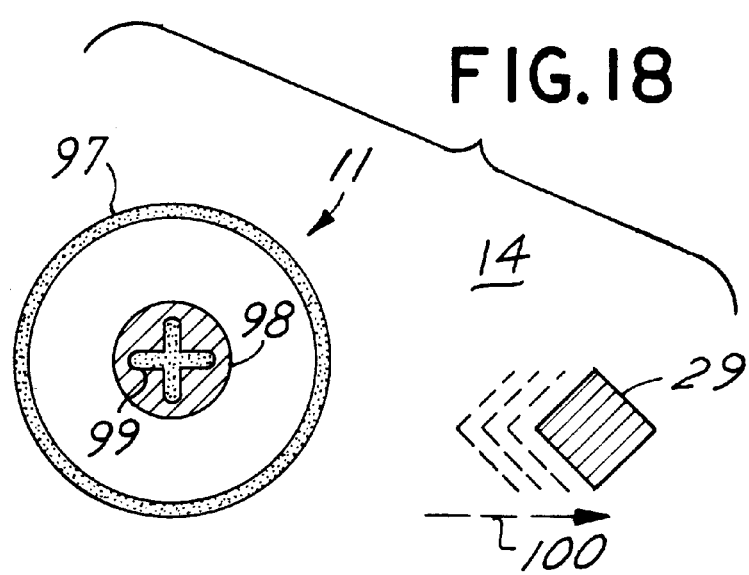
FIG. 18 illustrates example temporal movement of the test symbol during the preferred embodiment of the blind spot pretest.
Figure 19:
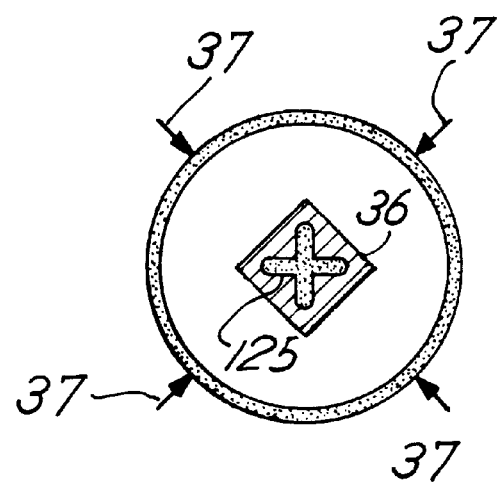
FIG. 19 illustrates an example event of the preferred color contrast acuity visual pretest.
Figure 20:
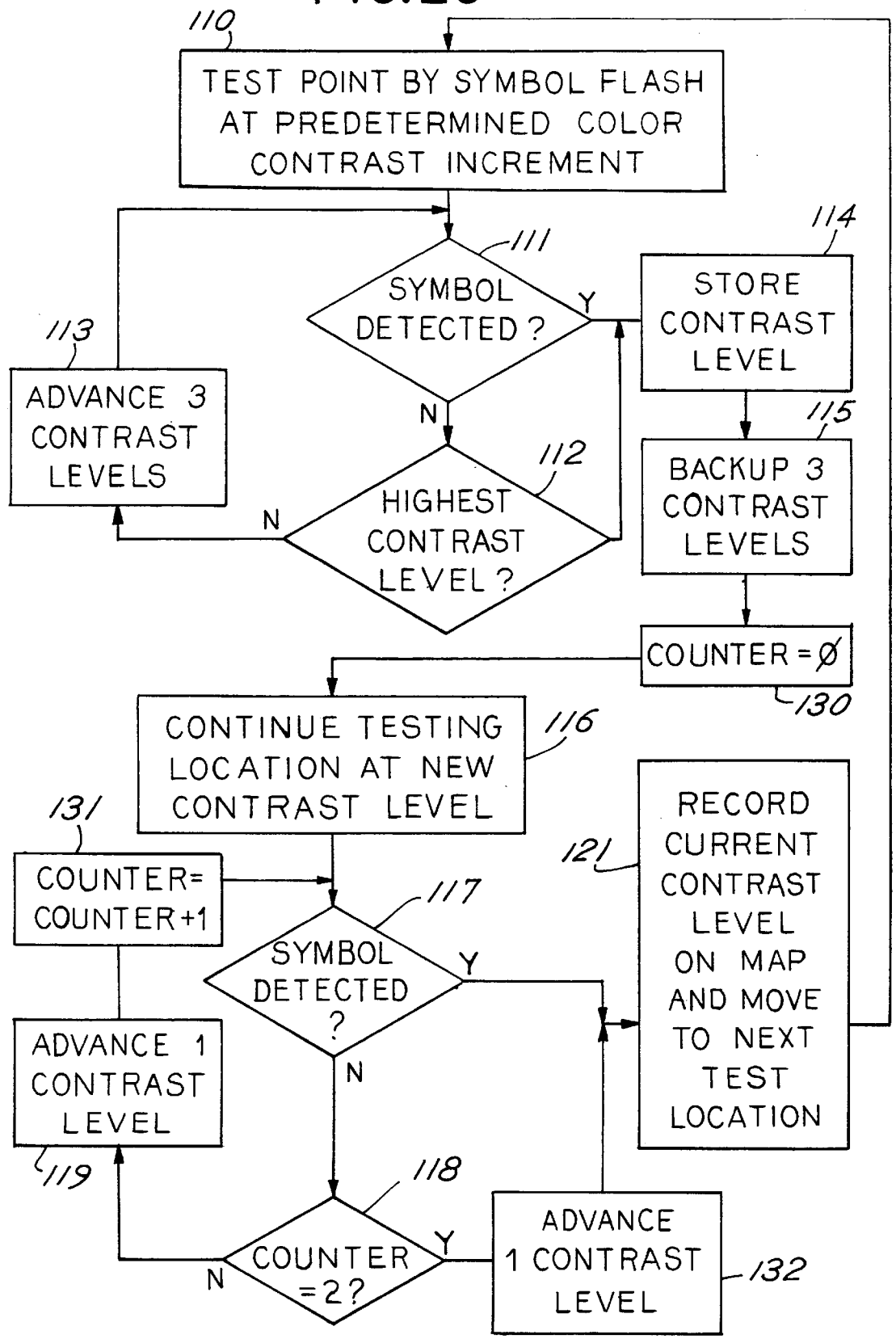
FIG. 20 is a chart showing generally the flow of the preferred professional mapping embodiment of the present invention.

In all vision tests involving side or peripheral vision testing, a fixation monitor or detector 11 is displayed in the center of the screen against a purple background 14, as is shown for example in FIG. 16. A pair of cross hairs 99 are disposed at the center of a black ring 97. Together the ring and cross hair arrangement constitutes a fixation detector 11 and enforcement system. In particular, the detector in the preferred embodiment consists of a well defined black circle 97 of about 0.5 inches diameter (in the center of which is the desired point of fixation), central yellow dot or zone 98 of about 0.25 inches diameter centered within the ring 97, and four peripheral radial arrows 96 pointing inward and touching tangentially the defined ring 97. Central cross-hairs 99 are superimposed over the yellow dot 98, such cross-hairs moving in synchronous fashion with movement of the computer mouse 4.

More particularly, the mouse cursor is synchronized to adjust the location of the cross-hairs 99 (the mouse cursor mark 125 is replaced with the cross-hair mark 99). The cross-hairs 99 are initially superimposed over the ring 97 and dot 98 configuration that "floats" (94) in a slow, repetitive vertical followed by horizontal motion. The defined circle 97 and central yellow dot 98 float slowly in a vertical and then horizontal range of slightly more than 100 pixels at 1 degree per 3 seconds (slightly more than the diameter of the yellow zone 98); the result being the cross hairs 99 will not remain in contact with the yellow dot 98 unless the computer mouse 4 is constantly slowly being moved by the test subject 9 to stay in synch. This speed can be adjusted, if desired. Moreover, the region within the black circle 97 preferably constitutes the entire universe in which the cross-hairs 99 may be moved, regardless of the extent of movement of the computer mouse, so that location and positioning of the cross-hairs 99 on the yellow dot 98 remains a relatively simple task for the test subject. Further, the size of the yellow dot 98 used is preferably larger in proportion to the higher age of the test subject.

Unless the test subject adjusts the cross-hairs 99 through manipulation of the computer mouse 4, the cross-hairs 99 will within a few seconds no longer be placed within the central yellow dot 98 (step 86), and the test is interrupted (87). The subject 9 must maintain the cross-hairs 99 on the moving central yellow dot 98, a rather small region of the test field 14, to avoid an interruption (87) in the testing procedure. Proper control of the mouse 4 causes the test program to proceed (93). If during testing the subject 9 loses focus and, in turn, causes the cross-hairs 99 to stray away from the yellow dot 98 and approach the boundaries of the fixation target 11 (step (91), the fixation target 11 flashes or otherwise indicates to the test subject 9 that the mouse cursor is straying (step (92). If the cross-hair 99 is not then repositioned appropriately the testing is suspended (step (87) and the test repeats itself (step (89) after appropriate instruction (step 88) to the test subject 9. Arrows 96 spaced around the outside of the black ring 97 point in an inward direction and arc or rotate around the ring 97 as an additional visual aid that draws attention to the focusing target to indicate to the test subject 9 that the test subject 9 should be prepared to maintain focus within the fixation monitor 11. A mechanism of this nature has been found to require a considerable degree of fixation for completion of the test. It can be further cause to eliminate occasional glances away, by controlling the speed of the floatation of the detector 11, and therefore the time it takes for a cross-hair 99 not being properly adjusted, to become out of sync.

Figure 13:
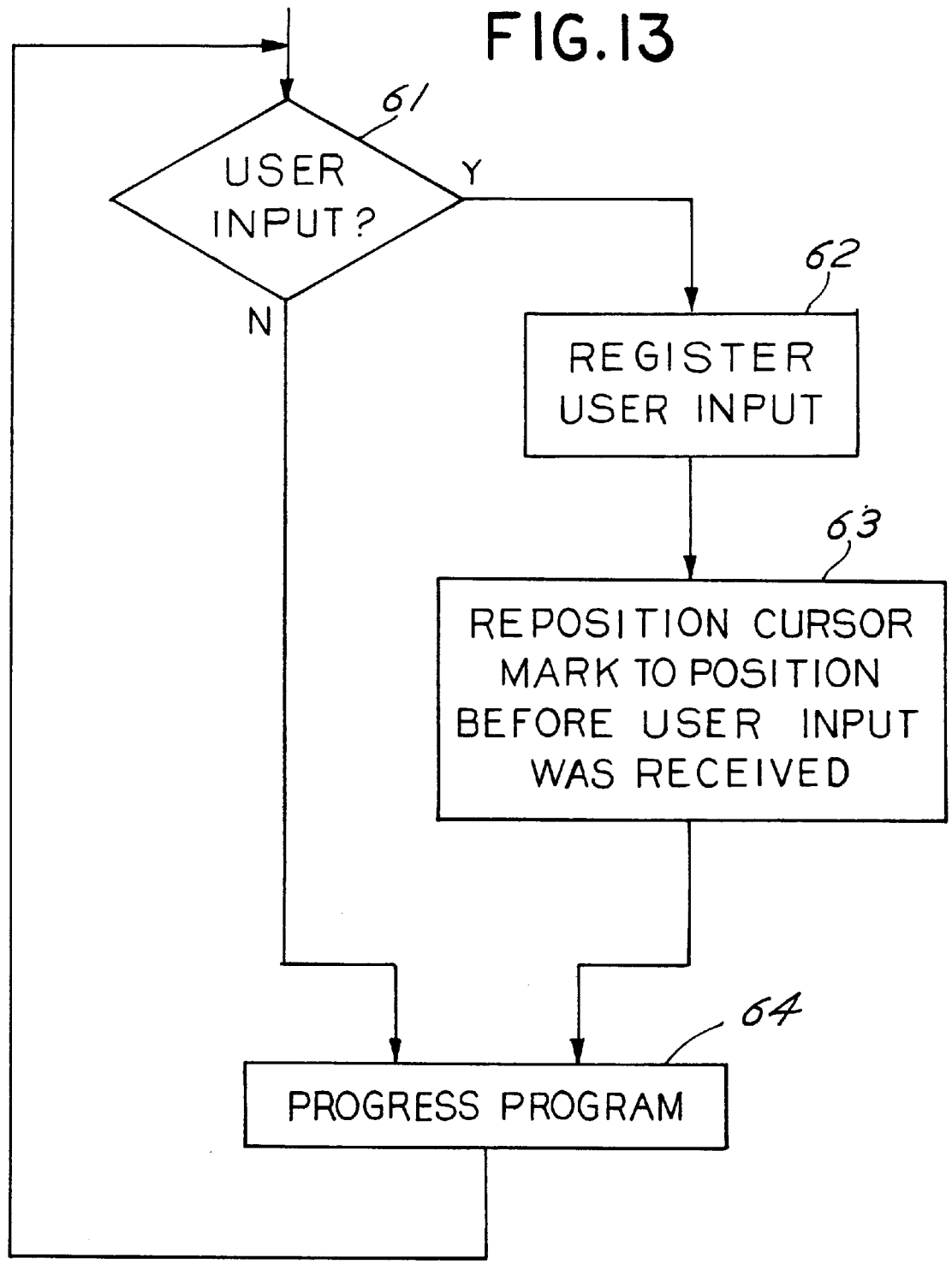
FIG. 13 is a chart showing generally the preferred flow of the cursor correction feature for the fixation detector aspect of the present invention.
Figure 14:
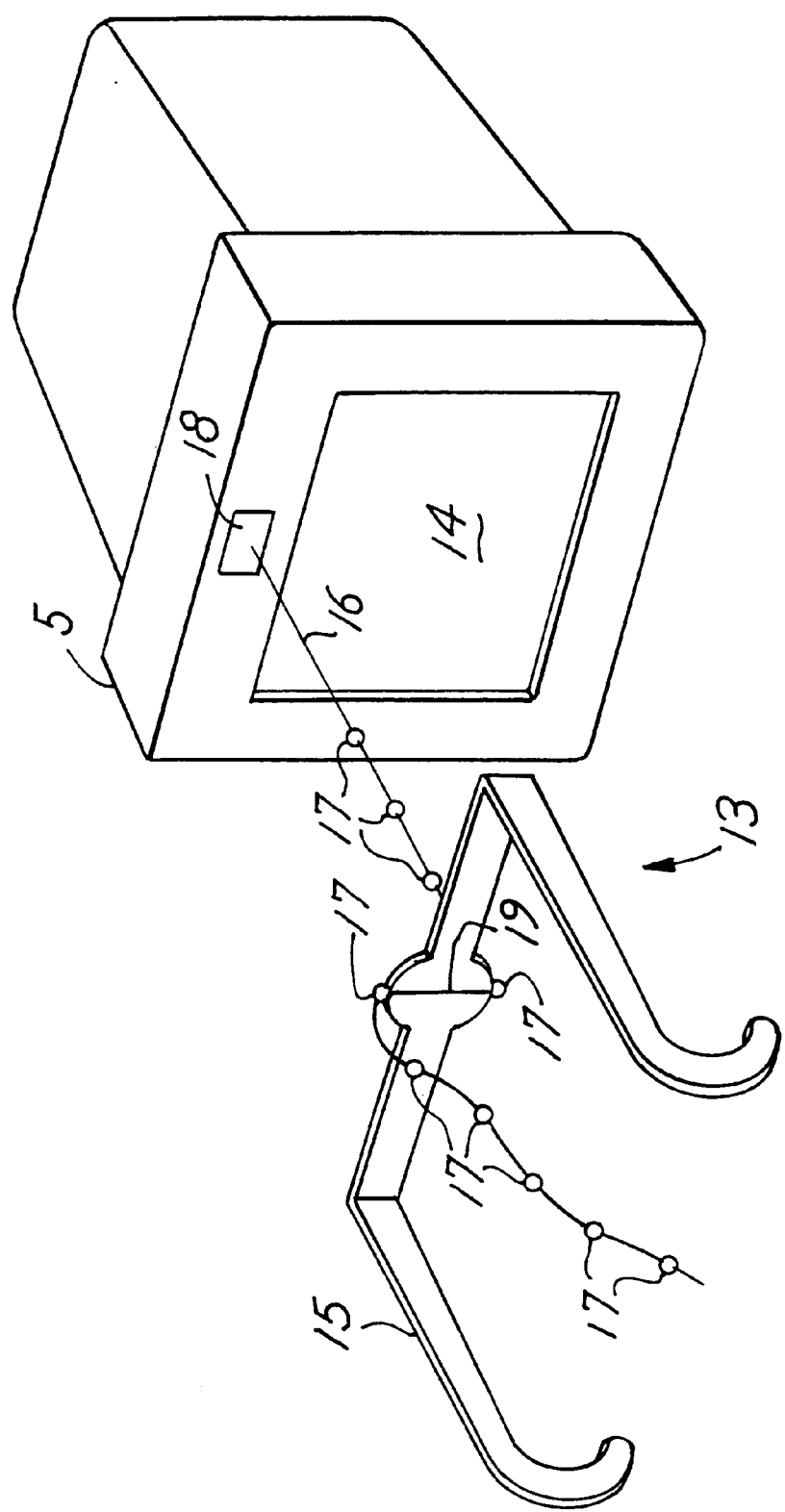
FIG. 14 illustrates a preferred distance prop for use in adjusting the test subject's position in front of the test field.
Figure 15:
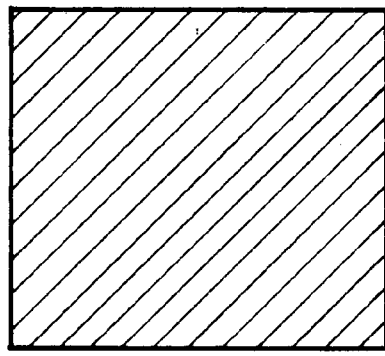
FIG. 15 shows a card that is used in the preferred embodiment of the present invention to help establish the appropriate ambient lighting conditions of the room in which the test is conducted.

As an additional aid, after each mouse click, as there may be inadvertent movement of the cross-hair cursor 99 from such a click, the cross hair 99 is automatically repositioned at its location prior to the click as compensation for this movement. The movement is thereby more stabilized, and the use of the fixation detector 11 is more simplified. This sequence of events is illustrated in FIG. 13, and represented by steps 61, 62, 63 and 64.

Conventional professional visual field tests in common use monitor fixation but do not induce or cause such fixation to be maintained. This novel feature of the present invention assists effective testing of peripheral vision, and aids in the desired accurate self-test realization. Increased attention paid to the fixation target 11 throughout the test improves the quality of the test results. This mechanism is therefore incorporated into each test of the preferred test program.

Blind Spot Vision Pretest

In the second vision pretest of the preferred embodiment, the second blind spot test (31), a blind spot mark 29 is presented for the test subject 9 in the central portion of the test field 14 (step 32), and gradually moved temporally away from the fixation target in a horizontal meridian about 2 degrees below the horizontal meridian of the fixation monitor for each eye (in a direction as shown by arrow 100) (step 33). The direction in which the mark 29 moves depends upon the eye being tested. If the right eye is being tested, the blind spot mark moves toward the right side of the test field 14. If the left eye is being tested, the blind spot mark moves toward the left side of the test field 14.

The test subject's responsibility is to indicate when the blind spot target 29 disappears from the test subject's view as the test subject synchronizes the mouse 4 with the fixation detector 11. A click on a computer mouse 4 is the preferred indicator for the disappearance of the blind spot target 29, although it will be understood that other types of indicators may be used instead. The test is repeated if the blind spot is not found, altering the horizontal meridian by 5 degrees, first below and if necessary above the original meridian, until the blind spot has been identified. In this way the pixel coordinates of the blind spot are identified, and then a distance adjustment advised, so as to fix the coordinates of each test taker to a region 12 that is the same relative distance between the monitor center and periphery. This ensures a consistent, similar cone angle of testing for each test taker.

The second blind spot pretest (31) is used to ensure that the test subject's blind spot located at a desired control region 12 of the test field 14, or, in other words, is associated with a particular set of display pixel coordinates. In particular, if as a part of step (34) it is determined that the presented blind spot target 29 has not disappeared from the test taker's field of vision by the time the blind spot target 29 moves beyond the desired blind spot region 12, then the test subject 9 is advised to move closer to the display 5. On the other hand, if the blind spot target 29 disappears from the test taker's field of vision before the blind spot target 29 reaches the desired blind spot region 12, then the test subject 9 is advised to move farther away from the display 5 (step 36).

In this way the preferred test program identifies the nasal margin of the test subject's blind spot, and adjusts the test subject's position with respect to the test field 14 in an effort to obtain a relatively consistent set of pixel coordinates for all test subjects. Proper mapping or fixing of the test subject's blind spot to the testing field 14 helps ensure that the desired degree of field is tested, because the preferred test program does not screen within a zone of about 2–4 degrees surrounding the blind spot disc 12.

Based on the results of this blind spot test (31), the test program preferably advises the test subject 9 to either move closer to or away from the test field (step 36). An absolute or change in distance D may be recommended by the test program, and may be expressed in terms of inches or centimeters, or alternatively in units relating to the distance prop, such as numbers of foam cups or specified protrusions 17 on the eyewear string 16, for example. The blind spot pretest (31) takes approximately 15 seconds to complete.

Color Contrast Acuity Vision Pretest

The vision color contrast test (35) comprises a series of targets or marks 36 that are individually and sequentially flashed, each in a momentary fashion, on the test field within the black ring 97 of the fixation target 11 (step 38). The marks 36 are similar in shape to marks 8 previously described, and may be varied in terms of color contrast. The test subject's response is received and recorded (step 41). If the test subject's responses indicate that the test subject has failed this portion of the test (step 42), then the test program terminates and appropriately warns the test subject (step 49). Otherwise, the test program may continue appropriately (step 48).

The initial targets 36 flashed on the test field in the vision pretest have a strong color contrast relative to the test field or background 14. As the test progresses, the color contrast of the targets 36 relative to the test field 14 become weaker, so as to test the sensitivity of the test subject 9. Indicators, such as arrows 37, are provided on the test field 14 to indicate to the test subject that the targets 36 that the test subject 9 is required to spot during the course of the test will appear in the center of the test field 14.

This test (35) allows a manner of testing that assesses the visual health of the fovea, or central vision region. It is known that contrast testing, that is the ability of the central vision to discriminate degrees of blackness relative to a background, is often reduced before loss of actual visual acuity in high contrast situations, such as the standard vision testing in a formal eye examination known as snellen acuity determination. The ability to assess black and white contrast may not be as sensitive a form of contrast testing as one that relies instead on ability to discriminate color contrast relative to a background, with no change in "blackness" or "luminance". The current invention therefore assesses the color contrast discriminating ability of the fovea, or central vision, by flashing objects 36 within the center of the vision detector 11, and requiring a response any time such a flash is observed. Such testing allows identification of early nonspecific loss of visual health, including color blindness, cataract, glaucoma, diabetic eye disease, and other diseases causing vision loss, in some cases being severely reduced while the test subject still retains excellent vision in high contrast environments, and may not yet be aware of a visual deficit. Rather than test for difference in luminance, as is typically done with conventional contrast testing, the preferred embodiment tests the ability to detect difference in color contrast relative to the background for the central or foveal acuity. This may offer a more sensitive means of vision assessment, as cones may be affected in their ability to discriminate color contrast before loosing ability to discriminate black and white, or luminance variation, as well as a relative measure of final acuity for pass, fail or monitoring purposes. Varying color contrast through presentation of different flashed color contrast images 36 within the fixation detector 11 achieves a contrast acuity testing of visual acuity (step 42). The preferred vision color contrast foveal test takes approximately 20 seconds to complete.

Figure 5:
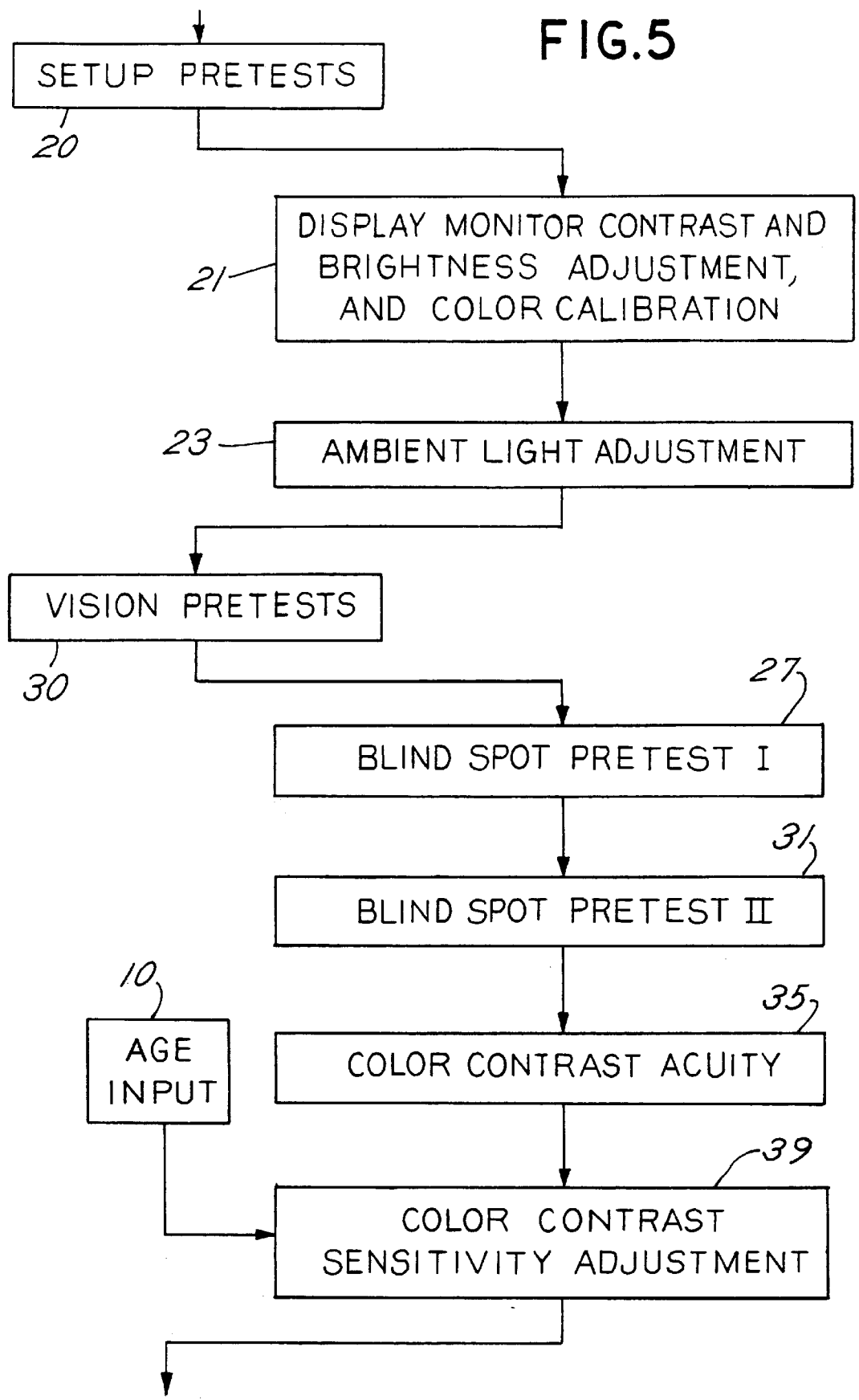
FIG. 5 is a chart showing generally the flow of the preferred setup pretests and vision pretests.
Figure 6:
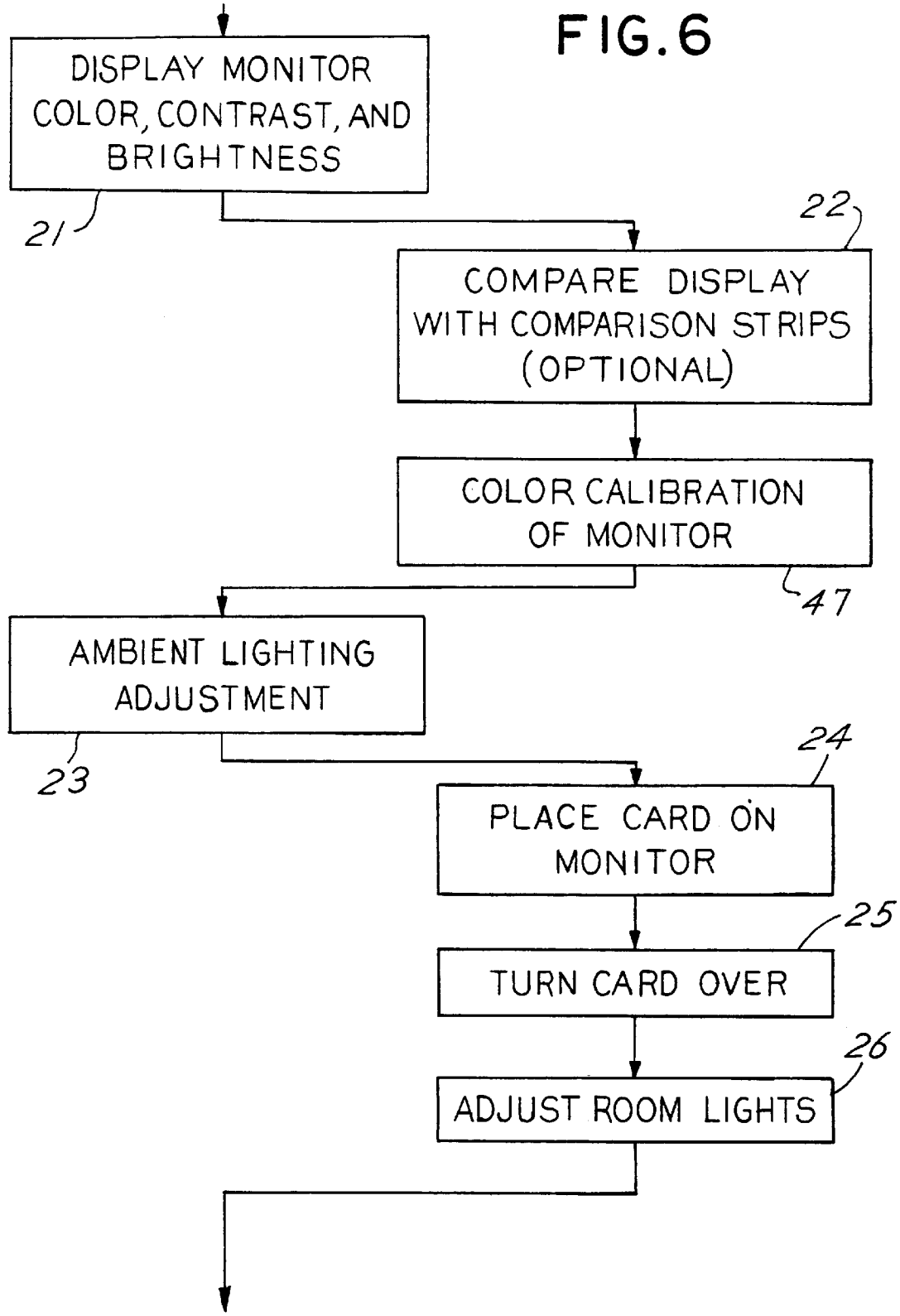
FIG. 6 is a chart showing generally the flow of the preferred display monitor and ambient lighting pretests.
Figure 7:
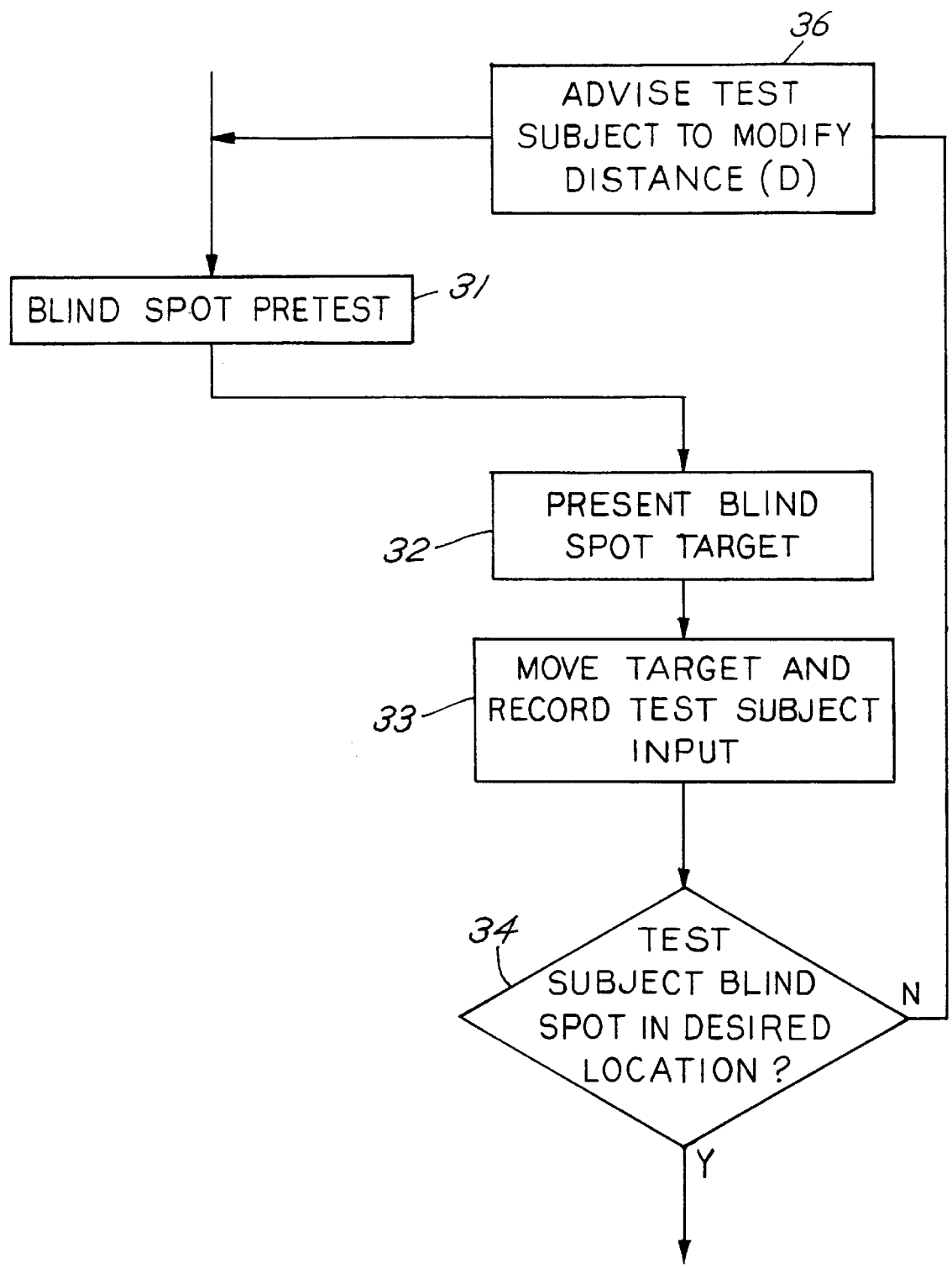
FIG. 7 is a chart showing generally the flow of the preferred blind spot pretest.
Figure 8:
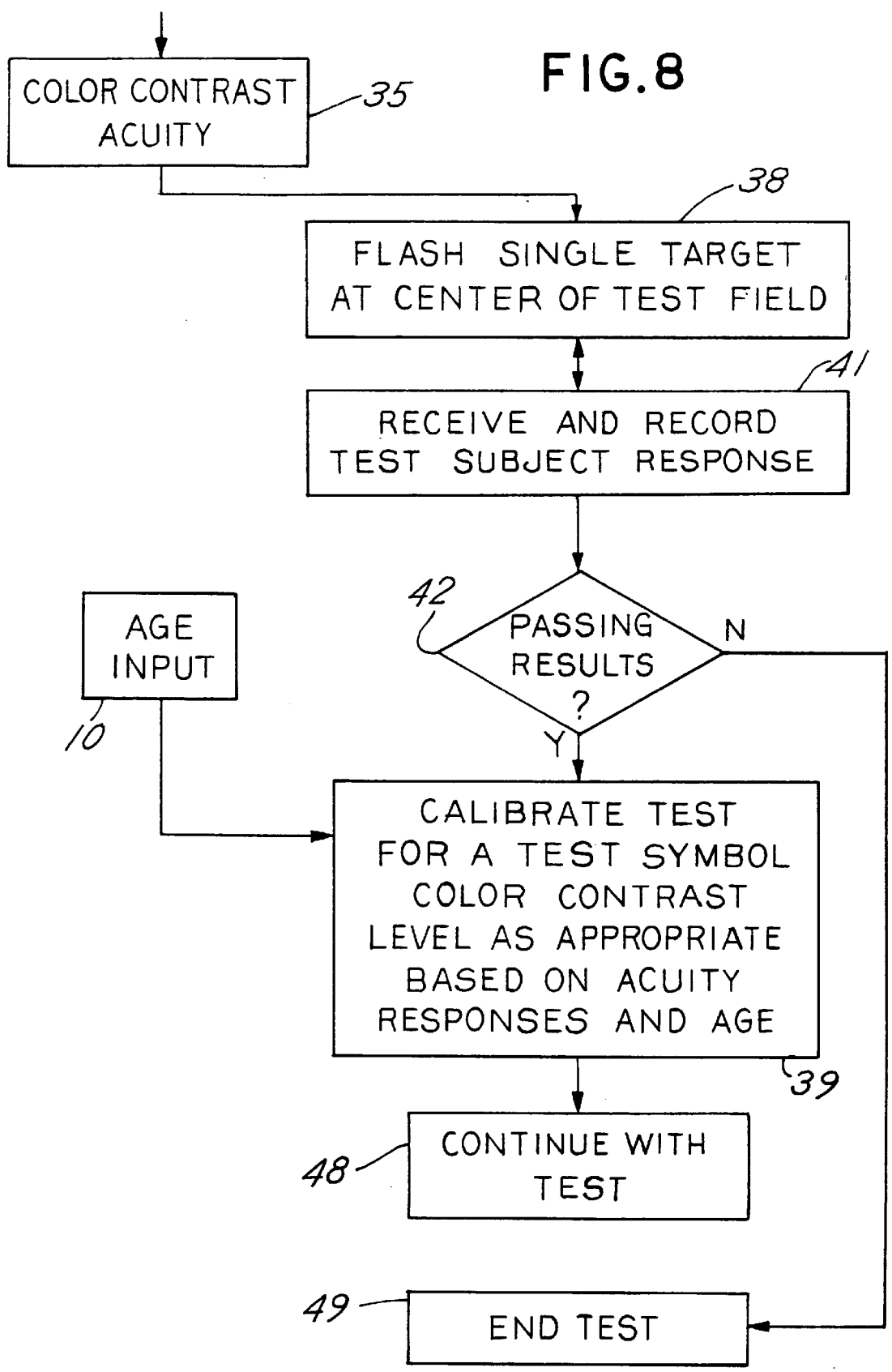
FIG. 8 is a chart showing generally the preferred flow of the color contrast acuity pretest.
Figure 9:
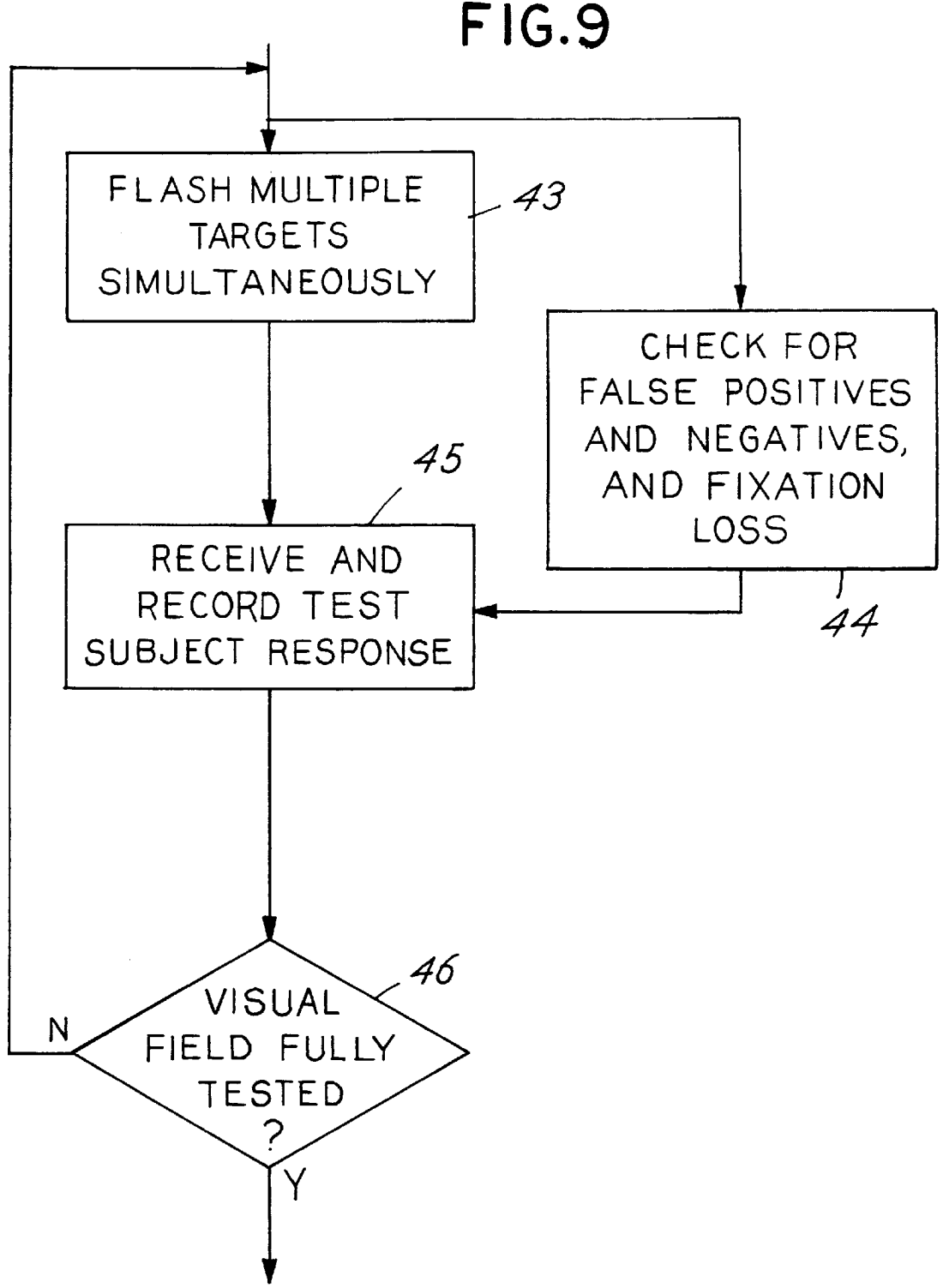
FIG. 9 is a chart showing generally the preferred flow of the multiple suprathreshold test.
Figure 10:
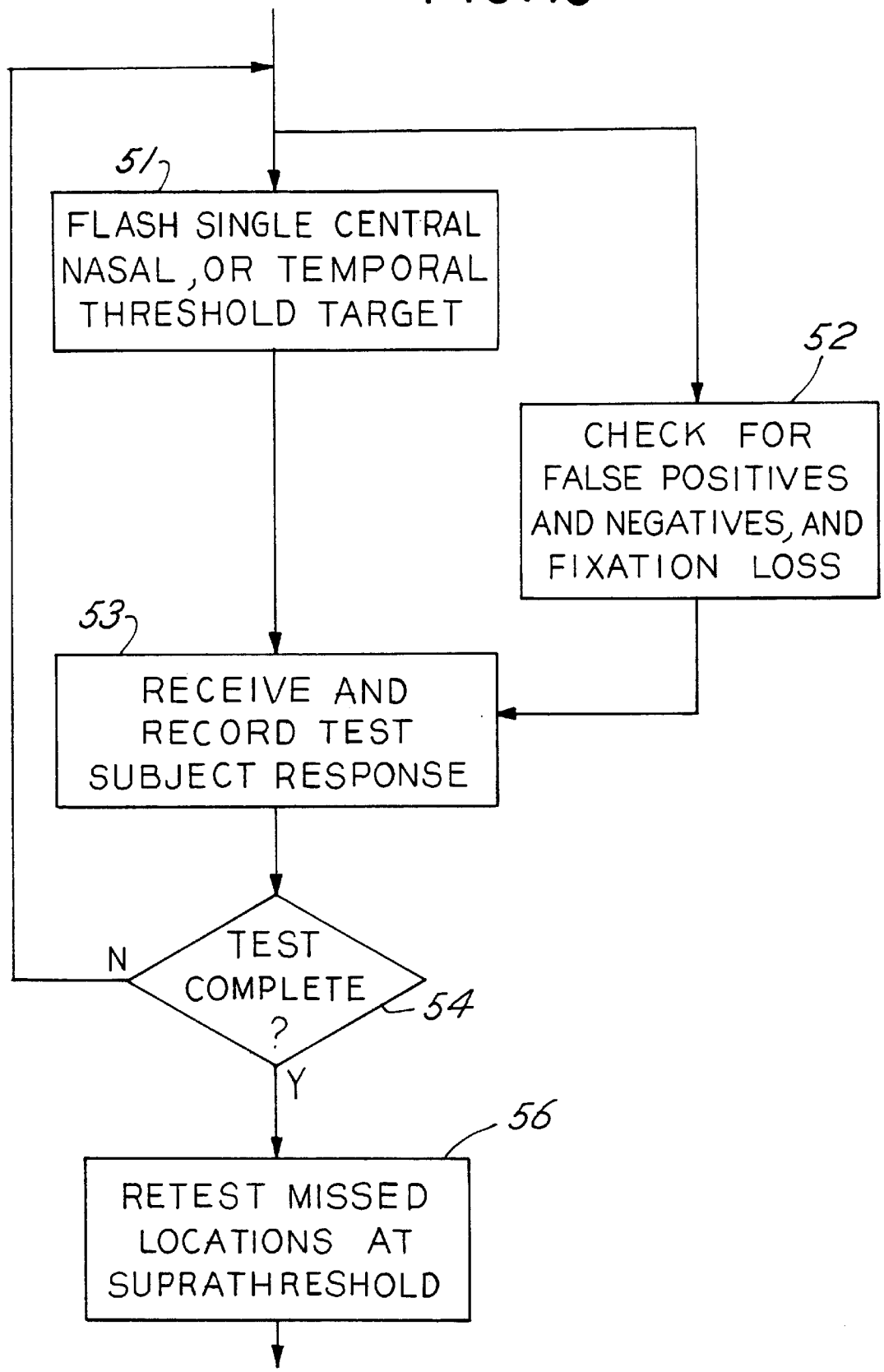
FIG. 10 is a chart showing generally the preferred flow of each of the central, nasal, and temporal single threshold tests.

Black and white or color contrast are both sensitive but non-specific indicators of disease, that are severely depressed when there is significant loss of visual field. The color contrast sensitivity of the test subject, as determined by the color contrast acuity vision pretest (35), may be used by the test program to adjust the color contrast of the test symbols 8 used during the remainder of the eye disease test sequence to a level that is deemed appropriate for the particular test subject, as is shown for example in step (39) set forth in FIG. 5, for either more accurate testing or monitoring purposes. The inputted age of the test subject, from step 10, may also be used to calibrate the color contrast sensitivity used during the test program.

Compliance

Moreover, by checking for false positive responses, false negative responses, and for fixation loss through presentation of symbols 8 in the blind spot region 12, (steps 44 and 52 for example), the vision pretests, as well as the other tests in the preferred test program, may also be used to determine generally the aptitude of the test subject 9 in taking tests of this nature. False positives are assessed by placing large objects, with nearly 200% color saturation, in or adjacent to foveal vision. Failure to indicate awareness of this flash when it is seen, constitutes a false positive error. Measuring foveal color contrast vision in the preceding test allows distinction between extremely advanced eye disease and false positive, as it is known whether the test taker can discriminate the very high color contrast object used for false positive compliance assessment. False negatives are assessed by placing sections within the test where no objects are flashed, and assessing whether any responses are made— acknowledging presence of a flash when none occurs would be known as a false negative response. Placing objects within the blind spot region 12 assessed and adjusted to earlier in the test further allows monitoring of fixation compliance. A further measure of false negatives is the number of responses made versus test symbols 8 or 36 presented—where for example the number of mouse clicks exceeds test symbols presented, in the preferred embodiment the test subject may be instructed to retake that test section, as too many mouse clicks are occurring. These test sequences are collated and scored separately as an indicator of test taking accuracy, known as compliance, that is standard to peripheral vision testing.

Multiple Suprathreshold Testing

A multiple suprathreshold test (40) optionally follows in the preferred test program to test for more advanced disease, insofar as one to three points well above threshold are selected for simultaneous testing. This test (40) takes only approximately two minutes to complete, because targets are presented in groups of one to three to allow for testing of many points in a short period of time. This test (40) is not included in the preferred test sequence, as it essentially parallels the single threshold test (60) results that follow. It has the potential advantage of allowing screening of many points in a short time frame.

The multiple suprathreshold test (40) is optionally administered by presenting the test subject 9 with a series of temporally-spaced, sequential events. Each event comprises a momentary and simultaneous flash of up to three targets or marks 8 presented on the test field 14 (step 43). The individual locations of the targets 8 on the test field 14 preferably vary from event to event, so as to ensure that all pertinent regions of the test subject's field of vision are sufficiently tested before the conclusion of the test (step 46). Moreover, the color contrast of the targets 8 presented within the same event may vary from target to target. Similarly, the color contrast of the targets 8 presented in two different events may be different.

The test subject 9 must try to discern the number of targets 8 presented in each flash. After each event the test subject 9 must identify the number of perceived targets. The perceived number of targets for each event may be recorded between events through the use of a computer mouse 4, whereby the test subject clicks a button on the mouse 4 in rapid succession; one click for each target 8 perceived (step 45). The test subject 9 is preferably given a period of approximately 200 milliseconds following the target flash in which to respond appropriately. In this preferred embodiment, the computer system 1 keeps track of the test results by monitoring the test subject's operation of the mouse button.

A complete multiple suprathreshold test (40) in the preferred test program consists of a succession of forty-three recorded events. Any differences between the number of targets 8 presented in a particular event and the number of targets perceived by the test subject 9 are noted.

27-Degree Nasal Test and 25-Degree Temporal Test

The preferred test program then conducts nasal and temporal single threshold tests (50 and 60) which test a field ($\alpha$) of approximately 20–27 degrees, thereby testing regions where some cases of earliest glaucoma change in the nasal test and/or tumor in the temporal test may occur. The preferred tests take only about 15 seconds each to complete. Placement of the fixation detector or target 11 is off-center as appropriate to increase the tested field ($\alpha$). The preferred tests again make use of the same fixation monitor 11 used in connection with the blind spot pretest. A purple background, or test field 14, is also used. Arrows 96 spaced around the outside of the black ring 97 point in an inward direction and arc or rotate around the ring 97 to indicate to the test subject 9 that the test subject 9 should be prepared to maintain focus within the fixation monitor 11. As with the other tests in the test program, the test subject 9 is instructed to remain focused on the fixation target 11 during the course of the test. The requirement that the test subject 9 maintain the computer mouse cursor mark 125/99 within the fixation target 11 throughout this test and other tests helps keep the test subject's attention focused, as described above.

In this test the black ring and cross-hair fixation target 11 described above is now presented in the vertical center of the test field 14, or on either the left side of the test field 14 or the right side of the test field 14, depending on whether the test is nasal or temporal, and on the eye being tested. If the right eye is being tested 27 degrees nasally, for example, the fixation target is presented on the right side of the test field 14. If the left eye is being tested in a similar nasal test, the fixation target is presented on the left side of the test field 14.

Only one target 8 is displayed for each event (step 51). The test subject 9 is presented in the preferred nasal threshold test with one hundred and fifteen events, the series of events being presented in a varying temporally-spaced sequence (step 54). While remaining focused on the fixation target 11, the test subject is required to indicate, by clicking once on the computer mouse 4 for example, when he or she perceives an event—i.e, the appearance of a target 8 (step 53). The test subject's responses to each event is recorded, and any events missed by the test subject 9 are noted. By moving the fixation target 11 off center, testing beyond 25 degrees of field occurs. It is the goal of the preferred embodiment to test at about 27 degrees maximum, as most useful visual field information, particularly for screening purposes, occurs inside this cone angle.

Any points tested as a part of the nasal and temporal threshold tests (50 and 60) where the test subject 9 provided inaccurate test responses are preferably retested at higher levels of color contrast, or at suprathreshold levels, to help determine the degree to which the test subject's vision is sub-standard at these particular locations (step 56). Preferably the level of color contrast that is used to retest the test subject 9 at these locations is adjustable, either manually or automatically in response to prior test results.

Central Threshold Test

The test program concludes with a central threshold test (65) of the central 25 degrees. The central single threshold test (65) tests vision just outside the fixation monitor 11 to about a 15 degree cone angle $\alpha$, such angle being that made from a line 122 from the visual axis of the test taker to the fixation detector 11, and a second line 123 from the test-taker to the peripheral-most points being tested.

The test subject 9 is again required to focus on the fixation target 11 and indicate, by clicking once on the computer mouse 4 for example, when he or she perceives the event—the momentary flash of a single mark 8. Instead of four rotating arrows, as in the multiple suprathreshold test, a single arrow arcs or rotates around the entire black ring 97 so as to indicate to the test subject 9 that he or she is supposed to, for each event, identify the appearance of a single target 8. The arcing of the single arrow about the ring 97 also indicates to the test subject 9 that the target 8 may be presented at any point on the test field 14. Testing in the preferred embodiment encompasses 1.7 degrees of separation, using a grid of about 65 test points known to be most common to losses in glaucoma, but covering sufficient area of visual field to be useful in identification of most forms of peripheral vision loss.

Again, any points tested as a part of the central threshold test (65) where the test subject 9 provided inaccurate test responses are preferably retested at higher levels of color contrast, or at suprathreshold levels, to help determine the degree to which the test subject's vision is sub-standard at these particular locations (step 56). Preferably the level of color contrast that is used to retest the test subject 9 at these locations is adjustable, either manually or automatically in response to prior test results.

The color contrast associated with the target flashes in any of the single threshold tests (50, 60, or 65) may vary from event to event. The average color contrast of the targets 8 presented in the single threshold tests (50, 60 and 65), however, is less than the average color contrast of the targets 8 presented in the multiple suprathreshold test (40). In this way the single threshold tests (50, 60 and 65) are more sensitive tests than the multiple suprathreshold test (40).

The single near threshold central, nasal, temporal tests of the preferred embodiment combined present the test subject with about 97 sequential events, taking approximately five minutes to complete not including time spent with the interactive learning feature of the preferred embodiment. Once again, the test subject's responses to each event is recorded, and any differences between the number of targets 8 presented in a particular flash and the number of targets 8 perceived by the test subject 9 are noted. Any missed points may be later tested at suprathreshold, a higher color contrast level (step 56).

ANALYSIS

Previously gathered data is used to determine the various points that should be tested and the contrast that should be administered at those locations such that 95% of the normal population will discern the contrast and identify that point. Since certain "normals" have modest visual field abnormalities, the threshold points may alternatively be selected to be either higher or lower than 95% to more closely reflect degree of Humphrey field loss. As there are some losses of sensitivity, reflex, and awareness due to age, adjustment of scoring can be made relative to age as well.

Dynamic data exchange may be used to score the test results, permit analysis of various test components, and to ultimately print out the results if desired. A data base may be used to allow scoring of the test results based on statistical comparison with large populations.

The test results may be presented in a variety of formats. For example, the test results may be presented by comparing the percent risk of eye disease of the test subject to the percent risk of eye disease for the test taker's age group. Certain test abnormalities, such as significant deficit on the nasal test, are more likely to be glaucoma related. Test subjects whose risk of eye disease, or more specifically glaucoma, is determined to be approximately average or above average can be directed to or presented with appropriate instructions and guidelines The preferred embodiment of the present invention provides, based upon the analysis of the quantified test results, one of the following indications to the test subject: "low risk"; "borderline/suspicious"; "high risk—professional evaluation required"; or "please retest—test not taken with sufficient accuracy". The latter indication is given to the test subject if the test subject's test compliance is deemed to be below average. The degree of test compliance is determined with reference to the test subject's particular variability in test results, incidence of false positive and/or negatives, as well as incidence of fixation loss.

While the preferred test program is administered through the use of conventional computer equipment, it will be understood to those of skill in the art that the present invention can alternatively be administered and otherwise presented, without departing from the true spirit and scope of the invention, using conventional color television monitors that display information received from broadcast or cable transmission, from a videocassette or laserdisk player, or some other like source. For this alternative embodiment, the computer mouse button responses described above may be replaced with, for example, verbal responses that are recorded by an individual acting as the test subject's partner, or by any other method that permits recordal of the test subject's responses for analysis.

Sensitivity and accuracy of the video format version of the present invention, however, can be maximized by using a blue/green format. Indeed, satisfactory results have been obtained using a 21-inch television monitor that displays peripheral test objects of uniform size, 0.75 inches$^2$.

A professional version of the test can be used in the medical office environment in accordance with the present invention, and may be used in conjunction with a computer or with video equipment for example. The preferred professional test again presents a central fixation target 11, as described above, against a purple test field, or background 14. Once the test subject's blind spot location has been fixed to the desired region 12 of the test field, as described above, the test program proceeds to test 125 different peripheral vision locations on the test field 14.

Figure 21:
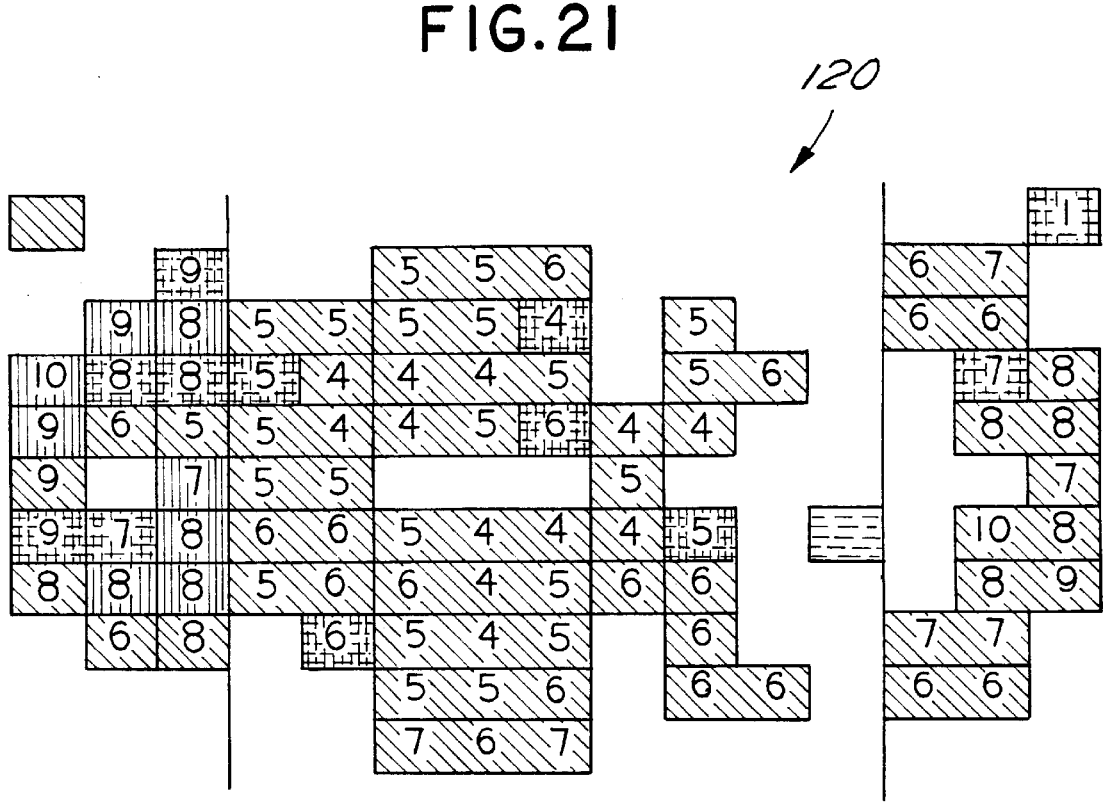
FIG. 21 is an example visual field map with numerical and color representations at each field point to indicate the test subject's threshold point at the various visual field locations.

The preferred professional test uses a computer system to provide a complete visual field test whereby 125 points in the visual field are tested sequentially and systematically with detailed quantification of threshold. The test is used to determine which of 14 increments of color level (color contrast relative to hue of background) is the lowest detectable color contrast for a given point in a visual field. The test is completed in approximately 4.5 minutes per eye for those with relatively healthy visual fields, and less than 6 minutes per eye in most other cases. A visual field threshold point map 120, such as the one shown for example in FIG. 21, can be displayed either on the computer monitor or printed in hard copy form, with the numerical values and/or color coding at each box or point tested to represent the threshold or relative color contrast increment detected at that location.

The preferred professional test consists of a series of identified grid coordinates. Each grid coordinate or point has a predetermined and age-matched starting color level, as determined through testing of normals within the various age groups. These predetermined color levels generally increase as the distance from the fovea increases, given that the threshold for detection of color contrast increases proportionally. The preferred test increases 3 color levels between steps, with each step constituting a 330 millisecond period in which a 50 millisecond flash of a color contrast symbol occurs 4–6 times over the 330 millisecond period. The preferred test therefore ramps up 9 color values in about 1 second (3 steps). As soon as a flash is first detected by the test subject, the test subject clicks a button on the computer mouse 4. Upon detection of this mouse click, the system ramps down from the detected color level by 3 color level increments. The test then continues in the same fashion, commencing with this reduced color level and having an increase of only 1 color value increment between steps rather than 3 color value increments as before.

By way of an example, a test point may begins testing at a predetermined color level of 4. A symbol having a color level of 4 flashes for 330 millisecond at 50 millisecond per flash (step 110). During the second 330 millisecond period, the color level increases to level 7 (113). The same flash timing and repetition rate is used. A color level of 10 is next used for the third 330 millisecond period (113), and the same flash repetition rate is again used. This continues until a test subject uses the computer mouse to transmit an indication to the computer that the flash has been detected (111), or until the highest end of the color level range is reached (112). If, for example, the test subject clicks the computer mouse during the second 330 millisecond interval at color level 7, the test stores the current level (114) and resets to color level 4 and resumes the testing (115 and 116), this time increasing for the second 330 millisecond period to color level 5 (119), and then color level 6 (119). If a click then occurs (117), the current color level of 6 is registered by the test program as the threshold for this test point (121). If no click occurs by the time color level 7 has been reached, the color level 7 will be recorded for the location (121).

Testing of all 125 points in this manner permits a threshold map 120 of the test subject's entire field of vision to be created for analysis purposes. Indeed, at the conclusion of the professional test a map 120 may be presented to indicate the test results. The preferred map 120, which is shown for example in FIG. 21, takes the form of a grid in which each of the various squares of the grid represents a location on the test field. Each square that relates to a tested location is filled with a number designation and color that each represent the test subject's threshold color contrast for that particular location.

For example, the preferred number scheme corresponds to the relative color contrast level increment discerned by the test subject at the various points tested, with the designation of "1" representing the most sensitive increment discernable as previously determined in a clinical setting. These are the same type of relative increments as previously discussed in the non-professional screening version of the test program. Similarly, green colors represent points that tested normal, while an orange color represents points that are suspect, and a red color represents points that are problematical.

The preferred vision screening test programs described above, professional or otherwise, may be modified to test for diabetic eye disease. Diabetic eye disease involves pathologic change to the retina, particularly that portion including the central vision, or foveal area, known as the macula. Diabetic eye disease causes macular dysfunction for a variety of reasons, including capillary drop out depriving vision receptors of necessary nutrition, background retinopathy damaging mechanically and/or optically through hemorrhage, exudate, or swelling from fluid leakage; or proliferative retinopathy in which neovascular and fibrovascular tissue can cause distortion/contraction of macular area(s) and/or bleeding.

In the preferred embodiment designed for the detection and monitoring of diabetic eye diseases, the test program that is described above for glaucoma testing purposes is converted to a macular field test, whereby a smaller cone angle is used to test only macular receptors. Macular receptors are where diabetic eye disease often occurs, and indeed must occur before the disease compromises the very central acuity, or foveal vision.

Testing of the macular field for diabetic eye disease is accomplished in this embodiment by positioning the test subject father away from the test field than the distance required for glaucoma testing. In this way the cone angle is reduced relative to the glaucoma test. The preferred distance D between the test subject and the test field for the diabetes screening is approximately twice the distance as determined by the blind spot pretest for the glaucoma screening. Doubling the separation distance results in a decrease in tested cone angle from 25 degrees to about 12.5 degrees. The use of a symbol presentation spacing that corresponds to the spacing required to place fifteen symbols equidistantly across the test field provides for testing for each 1.7 degree of field.

The optic nerve is approximately three millimeters in diameter, and represents about five degrees of field. The ability to test increments of one degree of field, as is provided by the preferred diabetes testing embodiment, helps to accurately detect macular pathology less than one millimeter in diameter.

Enlarging the stimulus size, such as to 90 $mm^2$ for example, can further enhance the sensitivity of the test by testing a large number of cones within each degree of field tested. Since there is a considerable gap between the color contrast that may be discernable by normals versus subjects with early diabetic pathology, a highly sensitive test can be conducted by selecting field points which are just above threshold.

Although certain embodiments of the invention have been described and illustrated, it will be readily apparent to those of ordinary skill in the art that a number of modifications and substitutions can be made to the method for detecting the presence of eye disease in a human eye disclosed and described herein without departing from the true spirit and scope of the invention.

I claim:

1. A method for screening for abnormalities in the field of vision of a test subject, comprising the steps of:

focusing an eye to be tested on a fixation target positioned on a colored planar surface;

positioning said test eye a separation distance from said fixation target and aligning said test eye relative to said fixation target to enable testing of said test subject's peripheral vision by adjusting the distance and alignment of said test eye relative to said fixation target with reference to a blind spot mark so that said blind spot mark is in a blind spot area outside of said test subject's area of central vision and is thereby removed from said field of vision of said test subject when said test eye is positioned and aligned for testing;

maintaining substantially said positioned and aligned test eye for the duration of testing in order to maintain said separation distance and said alignment of said test eye relative to said fixation target;

maintaining substantially said focus of said test eye on said fixation target for the duration of testing; and determining the visibility of additional marks employing the peripheral vision of the test eye, said additional marks being of low color contrast relative to said colored planar surface to form color contrast symbols, whereby the presence of eye disease is detected if said additional marks are not visible since the additional marks are presented with sufficient color contrast on the planar surface to be within the field of vision of a test subject's eye not having the disease.

2. The method of claim 1, wherein each of said additional marks is of the same size.

3. The method of claim 1, wherein said additional marks are momentarily presented on said planar surface for detection by said test subject.

4. The method of claim 3, wherein said additional marks are momentarily presented on said planar surface for approximately 50 milliseconds.

5. The method of claim 4, wherein each of said additional marks is of the same size.

6. The method of claim 3, wherein the planar surface is a display monitor.

7. The method of claim 1, further comprising the step of adjusting the lighting level of the room in which the test is being conducted with reference to a light meter.

8. The method of claim 7, wherein said light meter comprises a card having a region of luminescent material.

9. The method of claim 8, wherein said light meter further comprises a symbol printed on said card.

10. The method of claim 9, wherein said symbol comprises a set of light meter instructions printed on said card adjacent said region of luminescent material.

11. The method as set forth in claim 1, wherein the eye disease to be detected is diabetic eye disease, and wherein the separation distance between said eye of said test subject and said fixation target is being approximately one meter, and wherein said color contrast symbols are presented in a region corresponding to approximately a 10-degree cone angle.

12. A method for screening for abnormalities in the field of vision of a test subject, comprising the steps of:

presenting to said test subject a fixation target positioned on a colored planar surface, so that said test subject may focus a test eye on said fixation target and position said test eye a separation distance from said fixation target and align said test eye relative to said fixation target to enable testing of said test subject's peripheral vision by adjusting the distance and alignment of said test eye relative to said fixation target with reference to a blind spot mark so that said blind spot mark is in a blind spot area outside of said test subject's area of peripheral vision and is thereby removed from the test subject's field of vision when said test eye is positioned and aligned for testing; and presenting on said planar surface additional marks for detection by said test subject using the peripheral vision of the test eye, said additional marks being of low color contrast relative to said colored planar surface to form color contrast symbols, whereby the presence of eye disease is detected if said additional marks are not visible since the additional marks are presented with sufficient color contrast on the planar surface to be within the field of vision of a test subject's eye not having the disease.

13. The method of claim 12, wherein each of said additional marks is of the same size.

14. The method of claim 12, wherein said additional marks are momentarily presented on said planar surface for detection by said test subject.

15. The method of claim 14, wherein the planar surface is a display monitor.

16. The method of claim 15, wherein said display monitor is connected to a computer and wherein the focus of said test eye on said fixation target is facilitated by requiring the test subject to maintain a displayed cursor mark within said fixation target in order for the test to progress.

17. The method of claim 12, further comprising the step of providing a light meter for reference in adjusting the lighting level of the room in which the test is being conducted.

18. The method of claim 17, wherein said light meter comprises a card having a region of luminescent material.

19. The method of claim 18, wherein said light meter further comprises a symbol printed on said card.

20. The method of claim 19, wherein said symbol comprises a set of light meter instructions printed on said card adjacent said region of luminescent material.

21. The method as set forth in claim 12, wherein the eye disease to be detected is diabetic eye disease, and wherein the separation distance between said eye of said test subject and said fixation target is being approximately one meter, and wherein said color contrast symbols are presented in a region corresponding to approximately a 10-degree cone angle.

22. A method for testing the central vision of a test subject, comprising the steps of:

placing marks centrally on a planar surface, said central marks being of low color contrast relative to said planar surface; and determining sensitivity of said marks through direct viewing by said test subject through direct viewing of said marks.

23. A method for screening for abnormalities in the field of vision of a test eye of a test subject, comprising the steps of:

focusing said test eye on a fixation target positioned on a colored planar surface; and determining the visibility of objects flashed on the colored planar surface in the peripheral field of vision of said test eye, said flashed objects being of low color contrast relative to said colored planar surface to form color contrast symbols, whereby the presence of vision abnormalities are detected if said flashed objects are not visible since said flashed objects are presented with color contrast on said planar surface so as to be within the field of vision of an eye not having any abnormalities.

24. The method as set forth in claim 23, wherein at least one of said flashed objects has a different proportion of color relative to said colored planar surface as compared to other of said flashed objects.

25. The method as set forth in claim 24, wherein said flashed objects are of a geometrical shape.

26. The method as set forth in claim 23, wherein said colored planar surface and said flashed objects are colored using primary additive colors.

27. A method for screening for abnormalities in the field of vision of a test eye of a test subject, comprising the steps of:

identifying a peripheral field of said test eye relative to a colored planar surface;

flashing objects at locations on said colored planar surface within said peripheral field of said test eye, said flashed objects being of low color contrast relative to said colored planar surface to form color contrast symbols, and said flashed objects being presented with color contrast on said planar surface so as to be within the field of vision of an eye not having any vision abnormalities; and detecting the presence of vision abnormalities in said test subject by determining whether said flashed objects are visible to said test subject.

28. The method as set forth in claim 27, wherein at least one of said flashed objects has a different proportion of color relative to said colored planar surface as compared to other of said flashed objects.

29. The method as set forth in claim 28, wherein said flashed objects are of a geometrical shape.

30. The method as set forth in claim 27, wherein said colored planar surface and said flashed objects are colored using primary additive colors.

* * * * *